US008808626B2

(12) United States Patent
Miller et al.

(10) Patent No.: US 8,808,626 B2
(45) Date of Patent: Aug. 19, 2014

(54) AMPEROMETRIC IMMUNOSENSOR

(75) Inventors: Cary James Miller, Ottawa (CA); John Lewis Emerson Campbell, Woodlawn (CA)

(73) Assignee: Abbott Point of Care Inc., Princeton, NJ (US)

( * ) Notice: Subject to any disclaimer, the term of this patent is extended or adjusted under 35 U.S.C. 154(b) by 268 days.

(21) Appl. No.: 12/708,479

(22) Filed: Feb. 18, 2010

(65) Prior Publication Data
US 2010/0173396 A1 Jul. 8, 2010

Related U.S. Application Data

(62) Division of application No. 10/658,529, filed on Sep. 10, 2003, now Pat. No. 7,723,099.

(51) Int. Cl.
*G01N 27/00* (2006.01)
(52) U.S. Cl.
USPC ........ 422/82.01; 436/518; 436/524; 436/149; 422/50; 422/68.1; 435/7.1; 435/283.1; 435/287.1; 435/287.2
(58) Field of Classification Search
USPC ........ 436/518, 524, 149; 422/50, 68.1, 82.01; 435/7.1, 283.1, 287.1, 287.2
See application file for complete search history.

(56) References Cited

U.S. PATENT DOCUMENTS

| | | | |
|---|---|---|---|
| 3,853,467 A | 12/1974 | Giaver | |
| 4,280,815 A | 7/1981 | Oberhardt et al. | |
| 4,352,884 A * | 10/1982 | Nakashima et al. | 435/180 |
| 4,454,007 A * | 6/1984 | Pace | 205/778 |
| 4,584,130 A | 4/1986 | Bucci | |
| 4,619,754 A * | 10/1986 | Niki et al. | 204/403.1 |
| 4,686,479 A | 8/1987 | Young et al. | |
| 4,722,889 A | 2/1988 | Lee et al. | |
| 4,830,959 A | 5/1989 | McNeil et al. | |
| 4,908,115 A * | 3/1990 | Morita et al. | 204/403.1 |
| 4,959,307 A * | 9/1990 | Olson | 435/7.91 |

(Continued)

FOREIGN PATENT DOCUMENTS

| | | |
|---|---|---|
| DE | 19628002 | 12/1997 |
| EP | 0 397 424 | 11/1990 |

(Continued)

OTHER PUBLICATIONS

Chan, et al. "Development of a quantitative lateral-flow assay for rapid detection of fatty-acid binding protein", Journal of Immunological Methods, Elsevier Science Publishers B.V., Amsterdam, NL, vol. 279, No. 1-2, Aug. 2003, pp. 91-100.

(Continued)

*Primary Examiner* — Melanie Y Brown

(57) ABSTRACT

An electrochemical immunosensor system with reduced interference, comprising: a first immunosensor that generates an electrochemical signal based on the formation of a sandwich between an immobilized antibody, a target analyte and a labeled antibody, wherein a portion of the signal arises from non-specific binding of the labeled antibody in the region of the first immunosensor, and a second immunosensor that acts as an immuno-reference sensor and generates a signal that is the same as or predictably related to the degree of non-specific binding which occurs in the region of the first immunosensor, and has an immunocomplex between an immobilized antibody and an endogenous or exogenous protein that is in the sample and that is not the target analyte.

9 Claims, 14 Drawing Sheets

(56) References Cited

U.S. PATENT DOCUMENTS

| | | | |
|---|---|---|---|
| 4,980,065 A | 12/1990 | Hsu | |
| 4,997,526 A | 3/1991 | Robblee | |
| 5,063,081 A | 11/1991 | Cozzette et al. | |
| 5,079,142 A | 1/1992 | Coleman | |
| 5,081,063 A | 1/1992 | Vonno et al. | |
| 5,096,669 A | 3/1992 | Lauks et al. | |
| 5,112,455 A | 5/1992 | Cozzette et al. | |
| 5,156,953 A | 10/1992 | Litman | |
| 5,200,051 A | 4/1993 | Cozzette et al. | |
| 5,208,649 A | 5/1993 | Cuppoletti et al. | |
| D337,164 S | 7/1993 | Lauks et al. | |
| 5,254,315 A | 10/1993 | Nurse | |
| 5,256,315 A | 10/1993 | Lockhart et al. | |
| 5,447,440 A | 9/1995 | Daivs et al. | |
| 5,466,575 A | 11/1995 | Cozzette et al. | |
| 5,512,492 A | 4/1996 | Herron et al. | |
| 5,540,828 A * | 7/1996 | Yacynych | 205/198 |
| 5,554,339 A | 9/1996 | Cozzette et al. | |
| 5,628,961 A | 5/1997 | Davis et al. | |
| 5,638,828 A | 6/1997 | Lauks et al. | |
| 5,639,630 A | 6/1997 | Malin | |
| 5,653,243 A | 8/1997 | Lauks et al. | |
| 5,656,504 A | 8/1997 | Johansson et al. | |
| 5,666,967 A | 9/1997 | Lauks et al. | |
| 5,723,345 A | 3/1998 | Yamauchi et al. | |
| 5,753,519 A | 5/1998 | Durst | |
| 5,762,770 A | 6/1998 | Pritchard | |
| 5,779,650 A | 7/1998 | Lauks | |
| 5,807,752 A | 9/1998 | Brizgys et al. | |
| 5,821,399 A | 10/1998 | Zelin | |
| 5,824,268 A | 10/1998 | Bernstein | |
| 5,846,744 A * | 12/1998 | Athey et al. | 435/7.9 |
| 5,981,203 A | 11/1999 | Meyerhoff et al. | |
| 6,010,463 A | 1/2000 | Lauks et al. | |
| 6,030,827 A | 2/2000 | Davis et al. | |
| 6,087,088 A | 7/2000 | Piran et al. | |
| 6,106,778 A | 8/2000 | Oku et al. | |
| 6,159,681 A * | 12/2000 | Zebala | 435/4 |
| 6,180,417 B1 | 1/2001 | Hajizadeh et al. | |
| 6,274,872 B1 | 8/2001 | Katerkamp | |
| 6,287,438 B1 * | 9/2001 | Knoll | 204/409 |
| 6,287,451 B1 | 9/2001 | Winarta | |
| 6,322,963 B1 | 11/2001 | Bauer | |
| 6,346,387 B1 * | 2/2002 | Stewart et al. | 435/6.12 |
| 6,379,883 B2 | 4/2002 | Davis et al. | |
| 6,395,235 B1 | 5/2002 | Kilcoin et al. | |
| 6,436,699 B1 | 8/2002 | Berggren et al. | |
| 6,444,111 B1 * | 9/2002 | Montgomery | 205/334 |
| 6,451,610 B1 | 9/2002 | Gorman et al. | |
| 6,475,372 B1 | 11/2002 | Ohara et al. | |
| 6,478,938 B1 | 11/2002 | Paek et al. | |
| 6,509,196 B1 | 1/2003 | Brooks et al. | |
| 6,521,265 B1 | 2/2003 | Patterson | |
| 6,528,321 B1 | 3/2003 | Fitzgerald | |
| 6,670,115 B1 | 12/2003 | Zhang | |
| 7,018,848 B2 * | 3/2006 | Douglas et al. | 436/524 |
| 7,041,790 B2 | 5/2006 | Wescott et al. | |
| 7,078,167 B2 | 7/2006 | Delenstarr et al. | |
| 7,087,389 B2 | 8/2006 | Dhar et al. | |
| 7,297,312 B2 | 11/2007 | Ding et al. | |
| 7,332,327 B2 | 2/2008 | Vikholm et al. | |
| 7,338,809 B2 | 3/2008 | Yokoi | |
| 7,351,375 B2 | 4/2008 | Noda | |
| 2001/0029048 A1 | 10/2001 | Ding | |
| 2002/0068293 A1 | 6/2002 | Delenstarr | |
| 2002/0155033 A1 | 10/2002 | Strand et al. | |
| 2002/0155476 A1 | 10/2002 | Pourmand et al. | |
| 2003/0059954 A1 | 3/2003 | Vikholm | |
| 2003/0068665 A1 | 4/2003 | Kawamura et al. | |
| 2003/0082601 A1 * | 5/2003 | Dill | 435/6 |
| 2003/0207330 A1 | 11/2003 | Wescott | |
| 2004/0106190 A1 | 6/2004 | Yang et al. | |
| 2004/0209371 A1 | 10/2004 | Conlon | |
| 2004/0237663 A1 | 12/2004 | Farber | |
| 2005/0047972 A1 * | 3/2005 | Lauks et al. | 422/103 |
| 2005/0153459 A1 | 7/2005 | Kopf-Sill | |
| 2010/0167308 A1 | 7/2010 | Miller et al. | |
| 2010/0167312 A1 | 7/2010 | Miller et al. | |
| 2010/0167386 A1 | 7/2010 | Miller et al. | |
| 2010/0203550 A1 | 8/2010 | Miller et al. | |

FOREIGN PATENT DOCUMENTS

| | | |
|---|---|---|
| EP | 0420053 | 4/1991 |
| JP | S55-058166 | 4/1980 |
| JP | S64-026157 A | 1/1989 |
| JP | H02-501860 | 6/1990 |
| JP | H03-67171 | 3/1991 |
| JP | H03120467 | 5/1991 |
| JP | H05203607 | 8/1993 |
| JP | 5-273212 | 10/1993 |
| JP | 7-260782 | 10/1995 |
| JP | H09-143081 | 6/1997 |
| JP | H11-118794 A | 4/1999 |
| JP | 2000-065791 | 3/2000 |
| JP | 2000-321278 | 11/2000 |
| JP | 2000515966 | 11/2000 |
| JP | 2001-091512 A | 4/2001 |
| JP | 2001-318101 | 11/2001 |
| JP | 2001318180 | 11/2001 |
| JP | 2002501195 | 1/2002 |
| JP | 2002503331 | 1/2002 |
| JP | 2002-207022 | 7/2002 |
| JP | 2003501627 | 1/2003 |
| JP | 2003-507737 | 2/2003 |
| JP | 2003-294680 | 10/2003 |
| JP | 2003161733 A | 6/2006 |
| WO | WO 94/10573 | 5/1994 |
| WO | WO 0138873 | 5/2001 |
| WO | WO 01/14865 A1 | 11/2001 |
| WO | WO 02/10754 | 2/2002 |
| WO | WO 02/27316 | 4/2002 |
| WO | 02073203 | 9/2002 |
| WO | 03008956 | 1/2003 |
| WO | WO 03/019171 | 3/2003 |
| WO | WO 03/049860 | 6/2003 |
| WO | WO 03/058247 | 7/2003 |

OTHER PUBLICATIONS

Eddowes, "Direct Immunochemical Sensing: Basic Chemical Principles and Fundamental Limitations", Biosensors, 3: 1-15, 1987.

Laurell, "Electroimmunoassay", Methods in Enzymology, vol. 73, Academic Press, New York, 339, 340, 346-348, 1981.

Green, "Electrochemical Immunoassays", Phil. Trans. R. Soc. London, 316: 135-142, 1987.

Siegmann-Thoss, et al., "Enzyme Immunosensor for Diagnosis of Myocardial Infarction", Sensors and Actuators B, Elsevier Sequoia SA, Lausanne, CH, vol. 30, No. 1, Jan. 1996, pp. 71-76.

Supplemental European Search Report regarding EP 04809719, dated Oct. 21, 2008.

ISR and Written Opinion regarding PCT/US04/29498 dated Jul. 16, 2005.

Japanese Office Action with English Translation for Japanese Application No. 2006-526295 mailed Apr. 21, 2010.

Japanese Office Action for Japanese Application No. 2010-213233 mailed Dec. 13, 2011, 4 pages.

Vogelsang, et al., "Rheological Properties and Mechanical Stability of New Gel-Entrapment Systems Applied in Bioreactors," Biotechnol. Bioeng., 2000, vol. 70, No. 3, pp. 247-253.

Japanese Office Action for Japanese Application No. 2010-213232 mailed Dec. 27, 2011, 4 pages.

European Office Action issued in corresponding European Application No. 04809719.0-2404 mailed on Jul. 29, 2010.

Japanese Office Action with an English Translation issued in corresponding Japanese Application No. 2006-526295 mailed on Feb. 15, 2011.

Japanese Office Action with an English Translation issued in corresponding Japanese Application No. 2010-213231 mailed on Nov. 22, 2011.

(56) References Cited

OTHER PUBLICATIONS

Japanese Office Action with an English Translation only issued in corresponding Japanese Application No. 2010-213230 mailed on Feb. 15, 2011.
Japanese Office Action for JP2010-213231 dated Nov. 18, 2011.
Japanese Office Action for JP2010-213230 dated Nov. 22, 2011.
English language abstract for JP 2001-318180 A, Nov. 16, 2001.
English language abstract for JP 2002-503331 A, Jan. 21, 2002.
English language abstract for JP H05-203607 A, Jun. 21, 1990.
Japanese Office Action with English language translation for Japanese Application No. 2010-213230 mailed Feb. 15, 2011.
Japanese Office Action with English language translation for Japanese Application No. 2010-213231 mailed Mar. 15, 2011.
Japanese Office Action with English language translation for Japanese Application No. 2010-213232 mailed Mar. 15, 2011.
Japanese Office Action with English language translation for Japanese Application No. 2010-213233 mailed Mar. 15, 2011.
Canadian Office Action for Canadian Application No. 2,538,826 dated Jan. 21, 2010.

* cited by examiner

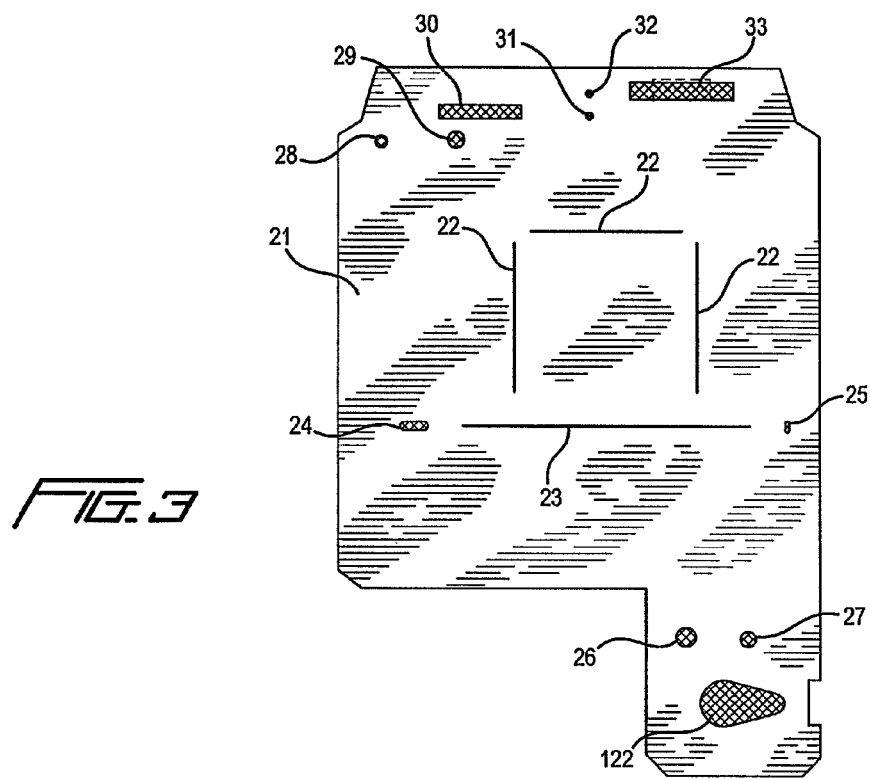
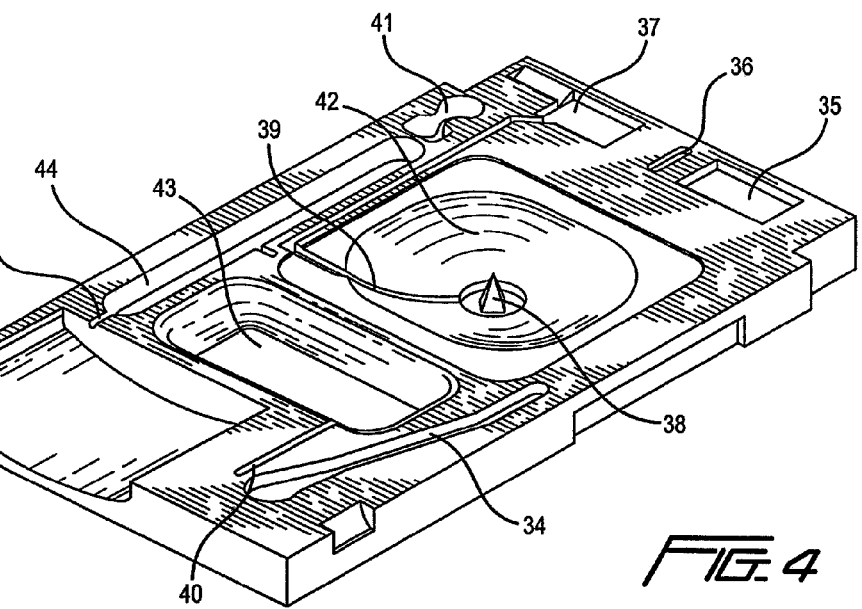

AMPEROMETRIC IMMUNOSENSOR

This application is a divisional of U.S. application Ser. No. 10/658,529, filed Sep. 10, 2003, now U.S. Pat. No. 7,723,099, which is incorporated herein by reference in its entirety.

I. FIELD OF THE INVENTION

An apparatus and method for rapid in situ determination of analytes in liquid samples that is capable of being used in the point-of-care clinical diagnostic field, including use at accident sites, emergency rooms, in surgery, in intensive care units, and also in non-medical environments.

II. BACKGROUND OF THE INVENTION

The invention relates to an apparatus and its method of use for determining the presence or concentrations of analytes in a liquid sample with single-use disposable cartridges adapted for conducting diverse real-time or near real-time assays of analytes.

In specific embodiments, the invention relates to the determination of analytes in biological samples such as blood using electrochemical immunosensors or other ligand/ligand receptor-based biosensors. The invention further relates to a reference-immunosensor for use with an immunosensor to reduce the effect of interferences in an immunoassay, it also relates to reducing the effect of cellular components, including leukocytes and erythrocytes, on an immunoassay performed in a whole-blood sample.

A multitude of laboratory tests for analytes of interest are performed on biological samples for diagnosis, screening, disease staging, forensic analysis, pregnancy testing, drug testing, and other reasons. While a few qualitative tests, such as pregnancy tests, have been reduced to simple kits for the patient's home use, the majority of quantitative tests still require the expertise of trained technicians in a laboratory setting using sophisticated instruments. Laboratory testing increases the cost of analysis and delays the results. In many circumstances, delay can be detrimental to a patient's condition or prognosis, such as for example the analysis of markers indicating myocardial infarction. In these critical situations and others, it would be advantageous to be able to perform such analyses at the point of care, accurately, inexpensively, and with a minimum of delay.

A disposable sensing device for measuring analytes in a sample of blood is disclosed by Lauks in U.S. Pat. No. 5,096,669. Other devices are disclosed by Davis, et al., in U.S. Pat. Nos. 5,628,961 and 5,447,440 for a clotting time. These devices employ a reading apparatus and a cartridge that fits into the reading apparatus for the purpose of measuring analyte concentrations and viscosity changes in a sample of blood as a function of time. A potential problem with such disposable devices is variability of fluid test parameters from cartridge to cartridge due to manufacturing tolerances or machine wear. Zelin, U.S. Pat. No. 5,821,399 discloses methods to overcome this problem using automatic flow compensation controlled by a reading apparatus using conductimetric sensors located within a cartridge. U.S. Pat. Nos. 5,096,669, 5,628,961, 5,447,440, and 5,821,399 are hereby incorporated in their respective entireties by reference.

Antibodies are extensively used in the analysis of biological analytes. For a review of basic principles see Eddowes, *Biosensors* 3:1-15, 1987. U.S. Pat. No. 5,807,752 to Brizgys discloses a test system in which a solid phase is impregnated with a receptor for an analyte of interest. A second analyte-binding partner attached to a spectroscopically-determinable label and a blocking agent is introduced, and the spatial distribution of the label is measured. Spectroscopic measurements require a light transducer, typically a photomultiplier, phototransistor, or photodiode, and associated optics that may be bulky or expensive, and are not required in electrochemical methods, in which an electrical signal is produced directly.

Electrochemical detection, in which binding of an analyte directly or indirectly causes a change in the activity of an electroactive species adjacent to an electrode, has also been applied to immunoassay. For a review of electrochemical immunoassay, see: Laurell, et al., Methods in Enzymology, vol. 73, *"Electroimmunoassay"*, Academic Press, New York, 339, 340, 346-348 (1981).

U.S. Pat. No. 4,997,526 discloses a method for detecting an analyte that is electroactive. An electrode poised at an appropriate electrochemical potential is coated with an antibody to the analyte. When the electroactive analyte binds to the antibody, a current flows at the electrode. This approach is restricted in the analytes that can be detected; only those analytes that have electrochemical midpoint potentials within a range that does not cause the electrode to perform non-specific oxidation or reduction of other species present in the sample by the electrode. The range of analytes that may be determined is extended by the method disclosed in U.S. Pat. No. 4,830,959, which is based upon enzymatic conversion of a non-mediator to a mediator. Application of the aforementioned invention to sandwich immunoassays, where a second antibody is labeled with an enzyme capable of producing mediator from a suitable substrate, means that the method can be used to determine electroinactive analytes.

Microfabrication techniques (e.g., photolithography and plasma deposition) are attractive for construction of multilayered sensor structures in confined spaces. Methods for microfabrication of electrochemical immunosensors, for example on silicon substrates, are disclosed in U.S. Pat. No. 5,200,051 to Cozzette, et al., which is hereby incorporated in its entirety by reference. These include dispensing methods, methods for attaching biological reagent, e.g., antibodies, to surfaces including photoformed layers and microparticle latexes, and methods for performing electrochemical assays.

In an electrochemical immunosensor, the binding of an analyte to its cognate antibody produces a change in the activity of an electroactive species at an electrode that is poised at a suitable electrochemical potential to cause oxidation or reduction of the electroactive species. There are many arrangements for meeting these conditions. For example, electroactive species may be attached directly to an analyte (see above), or the antibody may be covalently attached to an enzyme that either produces an electroactive species from an electroinactive substrate, or destroys an electroactive substrate. See, M. J. Green (1987) *Philos. Trans. R. Soc. Lond. B. Biol. Sci.* 316:135-142, for a review of electrochemical immunosensors.

The concept of differential amperometric measurement is well known in the electrochemical art, see for example jointly owned Cozzette, U.S. Pat. No. 5,112,455. In addition, a version of a differential amperometric sensor combination is disclosed in jointly owned Cozzette, U.S. Pat. No. 5,063,081. However, these and other references are silent on the concept of an immuno-reference sensor coated with antibody to a plasma protein, that is used in conjunction with an immunosensor for an analyte.

The prior art contains references to immunosensors for detection of human serum albumin using an antibody to human serum albumin for capture. These include Paek, (U.S. Pat. No. 6,478,938), Berggren (U.S. Pat. No. 6,436,699), Giaever (U.S. Pat. No. 3,853,467), Yamazoe (JP 07260782) and Owaku (JP 05273212). These references are silent on the use of anti-human serum albumin antibody, or other antibodies for establishing an immuno-reference sensor for use in conjunction with an immunosensor.

The following patents address various means for correcting an analytical determination for the effect of hematocit. U.S. Pat. No. 6,106,778 uses sample that is diluted and a Coulter-type cell counter to determine the erythrocyte cell count from which hematocrit is calculated. This is used to correct the result of an immunoassay. There is no anticipation of the use of a bulk conductivity sensor and an immunosensor, or making the measurements in undiluted blood. U.S. Pat. No. 6,475,372 teaches a method for correcting an analyte concentration for hematocrit based on two amperometric measurements at opposite polarities. U.S. Pat. No. 4,686,479 provides a sample ion correction for hematocrit measurements using the combination of an ion sensor and a conductivity sensor.

U.S. Pat. No. 5,081,063 discloses the use of permselective layers for electrochemical sensors and the use of film-forming latexes for immobilization of bioactive molecules, incorporated here by reference. The use of poly(vinyl alcohol) (PVA) in sensor manufacture is described in U.S. Pat. No. 6,030,827 incorporated here by reference. Vikholm (US 2003/0059954A1) teaches antibodies directly attached to a surface with a biomolecule repellant coating, e.g., PVA, the surface in the gaps between antibodies, and Johansson (U.S. Pat. No. 5,656,504) teaches a solid phase, e.g., PVA, with antibodies immobilized thereon. U.S. Pat. Nos. 6,030,827 and 6,379,883 teach methods for patterning poly(vinylalcohol) layers and are incorporated by reference in their entirety With regard to amperometric measurements, there are several means known in the art for reducing the importance of the non-Faradaic component of the signal, thus increasing sensitivity. These include newer electrochemical methods, e.g., using square wave voltammetry in place of chronoamperometry, and chemical means, e.g., an alkyl thiol reagent to passivate an electrode surface.

Various devices and methods for sealing a biological sample, e.g., blood into an analytical system for doing blood tests have been devised including; jointly owned Lauks, U.S. D 337,164; Lauks, U.S. Pat. No. 5,096,669; Lauks, U.S. Pat. No. 5,779,650; Lauks, U.S. Pat. No. 5,666,967; Lauks, U.S. Pat. No. 5,653,243; Lauks, U.S. Pat. No. 5,638,828 and Lauks, U.S. Pat. No. 6,010,463; as well as Cuppoletti, U.S. Pat. No. 5,208,649; Nurse, U.S. Pat. No. 5,254,315; Kilcoin U.S. Pat. No. 6,395,235 and Strand US 2002/0155033. However, these do not disclose a sealing element that is slidably movable over at least a portion of a planar surface to displace excess fluid away from a sample entry port, so as to seal a volume of fluid within a holding chamber and inhibit the fluid from prematurely breaking through a capillary stop.

III. SUMMARY OF THE INVENTION

One object of the invention is to provide an electrochemical immunosensor system with reduced interference, comprising:

a first immunosensor that generates an electrochemical signal based on the formation of a sandwich between an immobilized antibody, a target analyte and a labeled antibody, wherein a portion of the signal arises from non-specific binding of the labeled antibody in the region of the first immunosensor, and a second immunosensor that acts as an immuno-reference sensor and generates a signal that is the same as or predictably related to the degree of non-specific binding which occurs in the region of the first immunosensor, and has an immunocomplex between an immobilized antibody and an endogenous or exogenous protein that is in the sample and that is not the target analyte.

Another object is to provide a method for assaying a target analyte while reducing interference in an electrochemical immunosensor system, comprising:

contacting a sample containing a target analyte plus an endogenous or exogenous protein, which is not the target analyte, with an immunosensor system comprising a first immunosensor that generates an electrochemical signal based on the formation of a sandwich between an immobilized antibody, a target analyte and a labeled antibody, wherein a portion of the signal arises from non-specific binding of the labeled antibody in the region of the first immunosensor, a second immunosensor that acts as an immuno-reference sensor and generates a signal that is the same as or predictably related to the degree of non-specific binding which occurs in the region of the first immunosensor, and has an immuno complex between an immobilized antibody and said endogenous or exogenous protein, washing said first and second immunosensors with a wash fluid, and using the signal from the first immunosensor and the signal from the second immunosensor to determine a corrected analyte concentration in the sample.

Another object is to provide an immunoassay device for measuring an analyte in blood while reducing interference associated with leukocytes, comprising:

providing a conduit for receiving a whole-blood sample in an immunoassay device, said conduit containing a salt reagent and means for treating the sample sufficient to increase the ionic strength of the sample and thereby reduce interference from the buffy coat when the sample contacts the immunosensor.

Another object is to provide a method for measuring an analyte in blood in an immunoassay device while reducing interference associated with leukocytes, comprising:

adding a salt reagent to a whole-blood sample for an immunoassay device to increase the ionic strength of the sample and thereby reduce interference from the buffy coat when the sample contacts the immunosensor.

Another object is to provide an electrochemical immunosensor system for blood with reduced interference, comprising:

an immunosensor for blood samples that generates an electrochemical signal based on the formation of a sandwich between a first immobilized antibody to a target analyte, the target analyte, and a labeled antibody, wherein the sensing surface of said immunosensor contains a second immobilized antibody covering at least a portion thereof that forms an immunocomplex between an endogenous or exogenous protein that is in the sample and that is not the target analyte.

Another object is to provide an electrochemical immunoassay device for measuring an analyte in blood and correcting for the hematocrit of the sample to give an equivalent plasma analyte concentration, comprising:

providing a conduit for receiving a blood sample in an electrochemical immunoassay device, said conduit containing an immunosensor and a bulk conductivity sensor, providing computation means for processing signals from said sensors and determining the equivalent plasma analyte concentration.

Another object is to provide an amperometric immunosensor, comprising: an electrochemical sensing surface, for a blood sample, having a porous polyvinylalcohol layer patterned to cover at least a portion of the surface such that said layer attenuates background current from a blood sample to at least half the background current obtained in the absence of the layer.

Another object is to provide a method of performing an electrochemical immunoassay for an analyte in blood and correcting for the hematocrit of the sample, comprising:

(a) contacting an immunosensor with a blood sample, (b) contacting said blood sample with a bulk conductivity sensor and measuring its resistance, (c) contacting the immunosensor and conductivity sensor with an aqueous solution having known conductivity and containing reagents sufficient to generate a detectable product related to the amount of analyte bound to the immunosensor, (d) measuring the signal at the immunosensor generated by said product, (e) converting by means of an algorithm the signal from the immunosensor to an analyte concentration;

(f) calculating the hematocrit value of the blood sample from the measured resistance of the blood sample, and (g) correcting the calculated analyte concentration for the hematocrit of the sample.

IV. BRIEF DESCRIPTION OF THE DRAWINGS

These and other objectives, features and advantages of the present invention are described in the following detailed description of the specific embodiments and are illustrated in the following Figures in which:

FIG. 3 is a top view of the layout of a tape gasket for an immunosensor cartridge.

FIG. 4 is an isometric top view of an immunosensor cartridge base.

FIG. 9 is a top view of the mask design for the conductimetric and immunosensor electrodes for an immunosensor cartridge.

Figure 22:
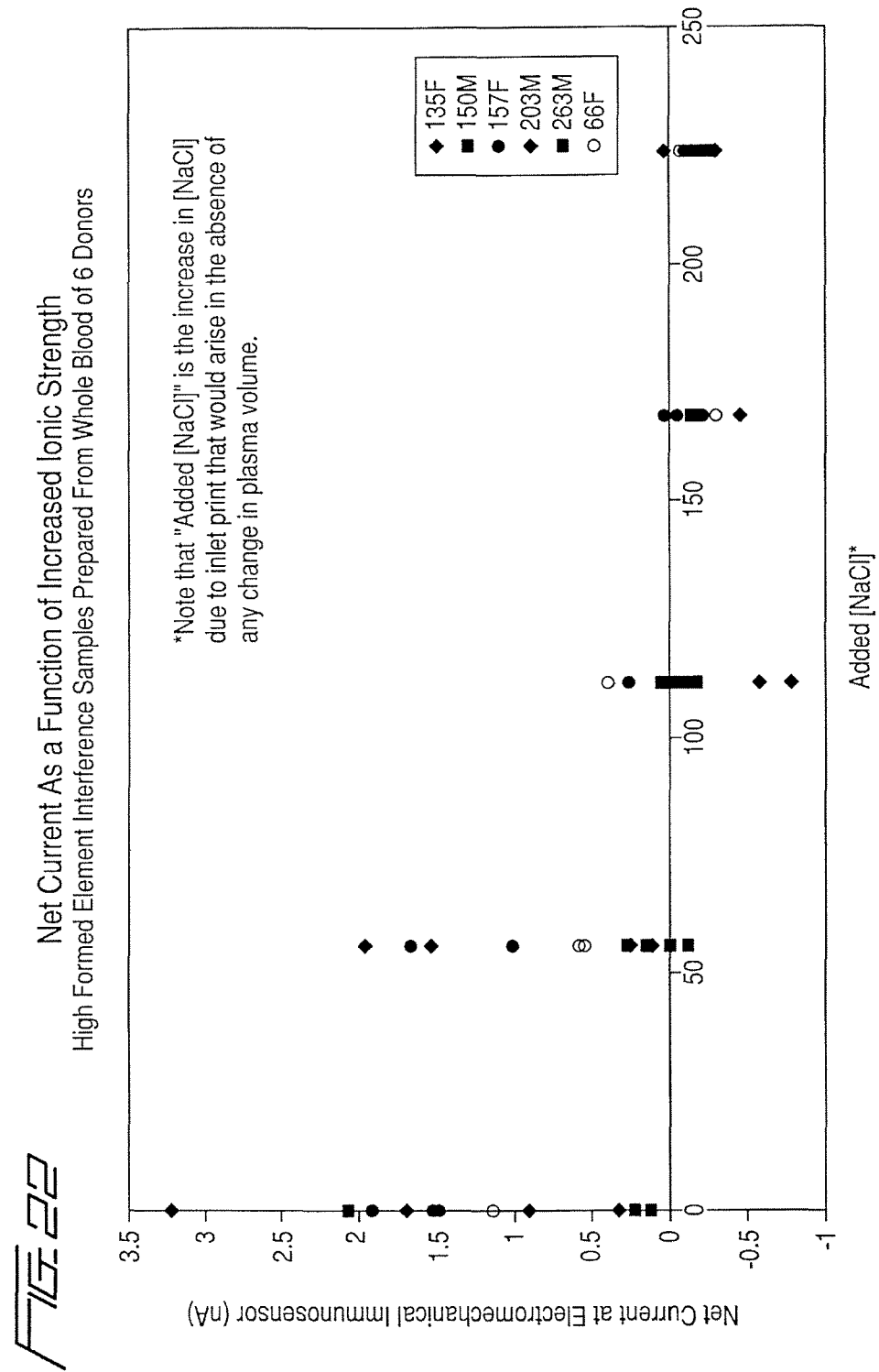

FIG. 22 illustrates the decreased background current at a troponin I immunosensor as a function of sodium chloride added to the sample. Addition of about 100 mM sodium ion brings the sample concentration to about 240 mM (assuming a typical blood sample sodium ion concentration of about 140 mM).

Figure 23:
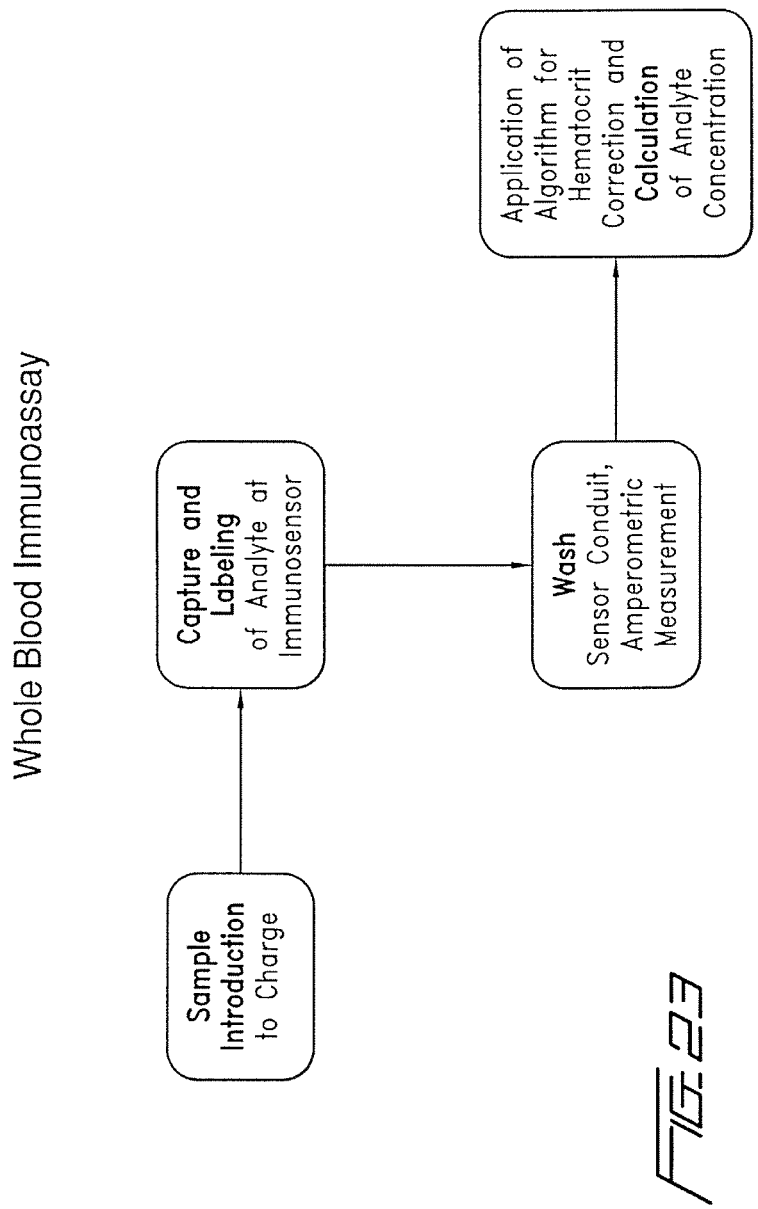

FIG. 23 is a schematic representation of a whole blood immunoassay.

Figure 24:
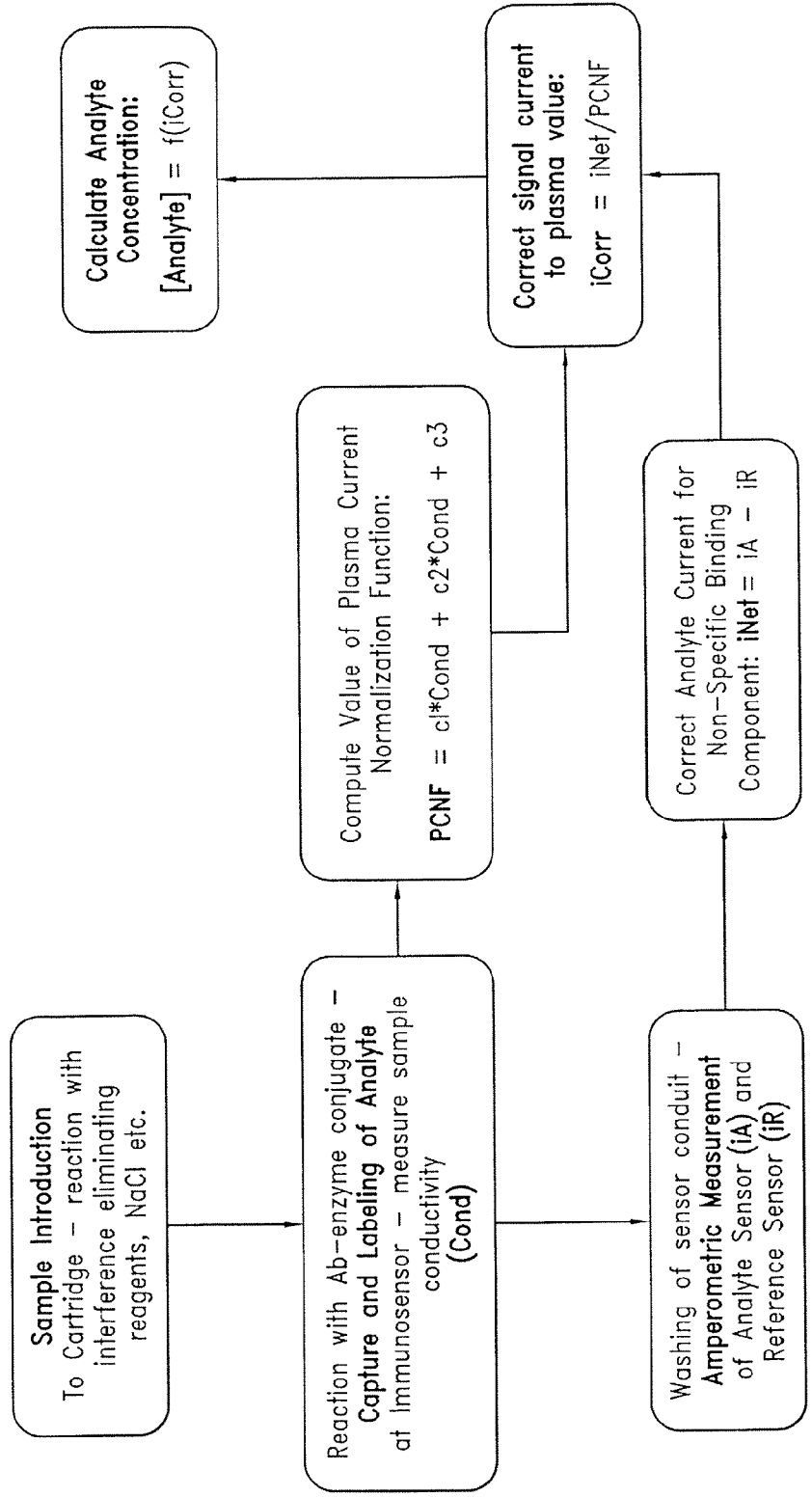

FIG. 24 is a schematic representation of a whole blood immunoassay with an immunoreference electrode.

V. DETAILED DESCRIPTION OF THE INVENTION

The present invention permits rapid in situ determinations of analytes using a cartridge having an array of analyte sensors and means for sequentially presenting a sample and a fluid (amended or not) to the analyte array. The cartridges are designed to be preferably operated with a reading device, such as that disclosed in U.S. Pat. No. 5,096,669 to Lauks, et al., issued Mar. 17, 1992, or U.S. Pat. No. 5,821,399 to Zelin, issued Oct. 13, 1998, which are both hereby incorporated by reference in their respective entireties.

The invention provides cartridges and methods of their use for processing liquid samples to determine the presence or amount of an analyte in the sample. The cartridges contain a metering means, which permits an unmetered volume of sample to be introduced, from which a metered amount is processed by the cartridge and its associated reading apparatus. Thus the physician or operator is relieved of accurately measuring the volume of the sample prior to measurement saving time, effort, and increasing the accuracy and reproducibility.

The metering means comprises an elongated sample chamber bounded by a capillary stop and having along its length an air entry point. Air pressure exerted at the air entry point drives a metered volume of the sample past the capillary stop. The metered volume is predetermined by the volume of the sample chamber between the air entry point and the capillary stop.

Slidable Closure

The cartridge may have a closure means for sealing the sample port in an air-tight manner. This closure device is slidable with respect to the body of the cartridge and provides a shearing action that displaces any excess sample located in the region of the port; reliably sealing a portion of the sample in the holding chamber between the entry port and the capillary stop. The cartridge is sealed by slidably moving a sealing element over the surface of the cartridge in a manner that displaces excess fluid sample away from the sample orifice, seals a volume of the fluid sample within the internal fluid sample holding chamber, and inhibits fluid sample from prematurely breaking through the internal capillary stop.

The seal obtained by this slidable closure means is irreversible and prevents excess blood from being trapped in the cartridge because the closure means moves in the plane of the orifice through which blood enters the cartridge and provides a shearing action that seals blood below the plane of the entry port; moving excess blood, i.e., blood above the plane of the orifice, away from the entry port and optionally to a waste chamber.

Figure 1:
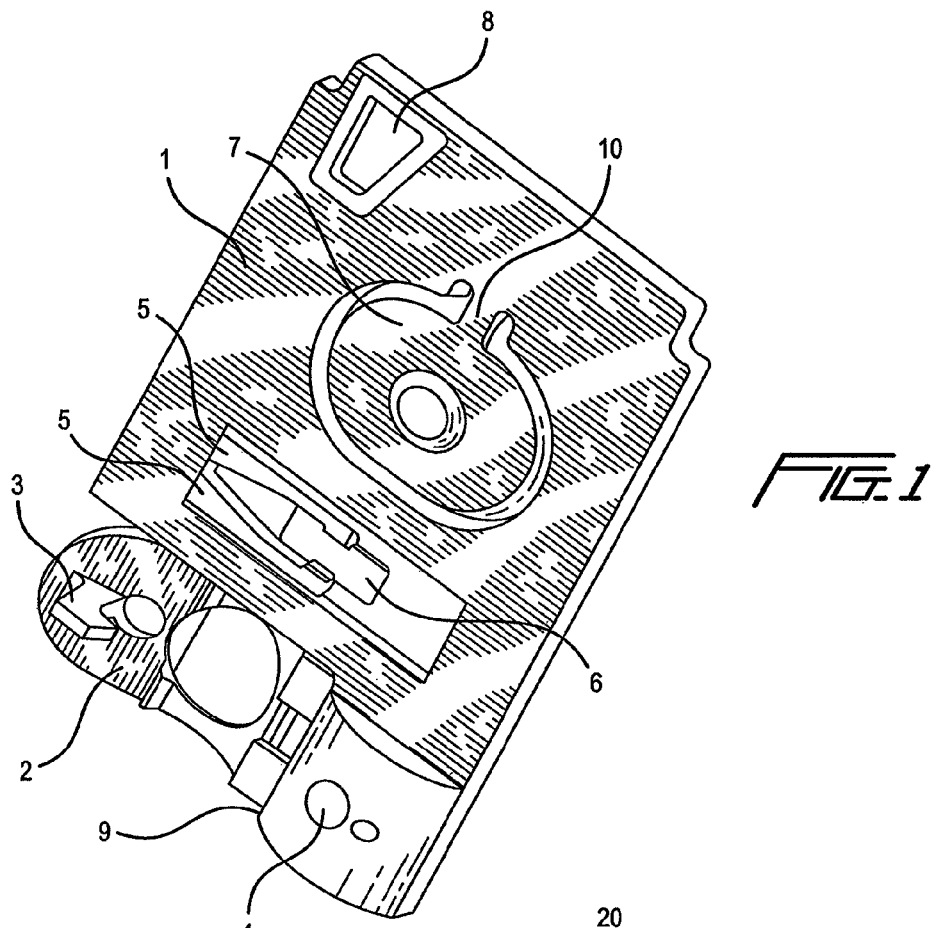
FIG. 1 is an isometric top view of an immunosensor cartridge cover.
Figure 18:
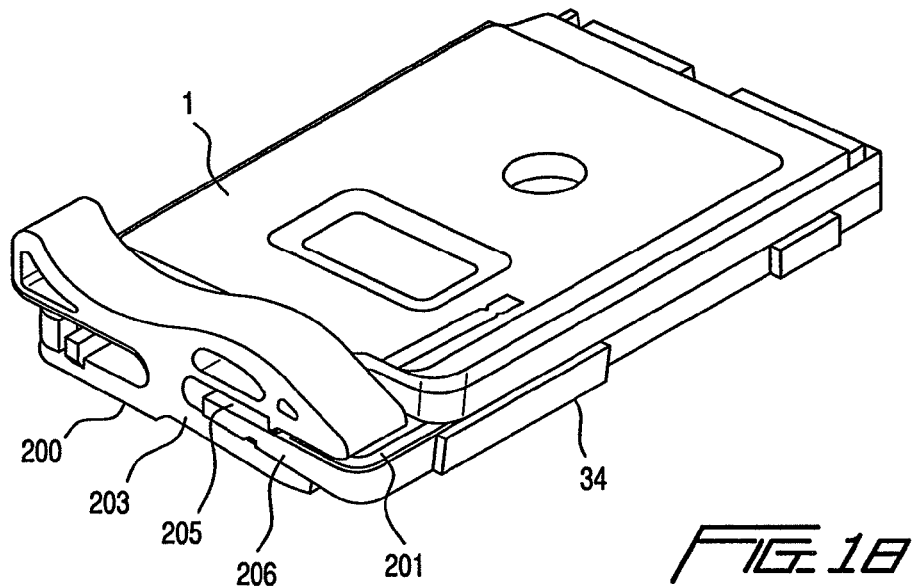
FIG. 18 illustrates the cartridge device with a slidable sealing element for closing the blood entry port in the closed position.
Figure 19:
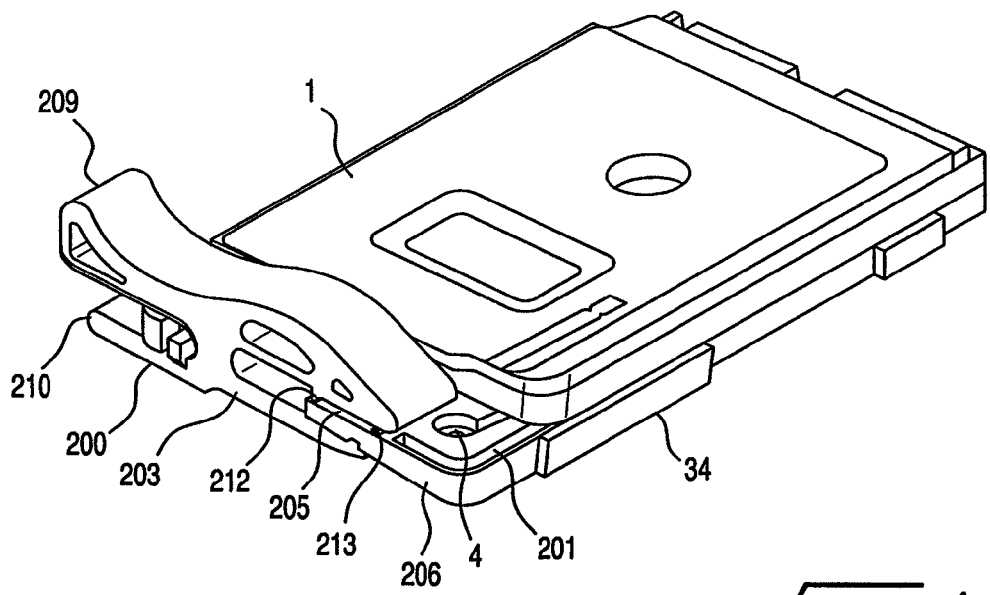
FIG. 19 illustrates the cartridge device with a slidable sealing element for closing the blood entry port in the open position.

Thus, an alternative to the blood entry port closure means comprising integrated elements 2, 3, 4 and 9 of cover 1 in FIG. 1 is shown as a separate slidable element 200 in FIGS. 18, 19, 20 and 21. FIG. 18 shows a cartridge device comprising a modified version of the cover of FIG. 1 attached to the base of FIG. 4 with the intervening adhesive layer 21 shown in FIG. 3 along with the separate slidable closure element 200. It is shown in the closed position where it seals the blood entry port in an air-tight manner. FIG. 19 shows the same components as FIG. 18, but with the slidable closure element in the open position, where the blood entry port 4 can receive blood. In operation, element 200 is manually actuated from the open to the closed position after blood has been added to the entry port and it enters the holding chamber 34. Any excess blood in the region of the entry port is moved into an overflow chamber 201 or an adjacent retaining region. This chamber or region may include a blood-absorbing pad or material to retain the excess blood.

Figure 20:
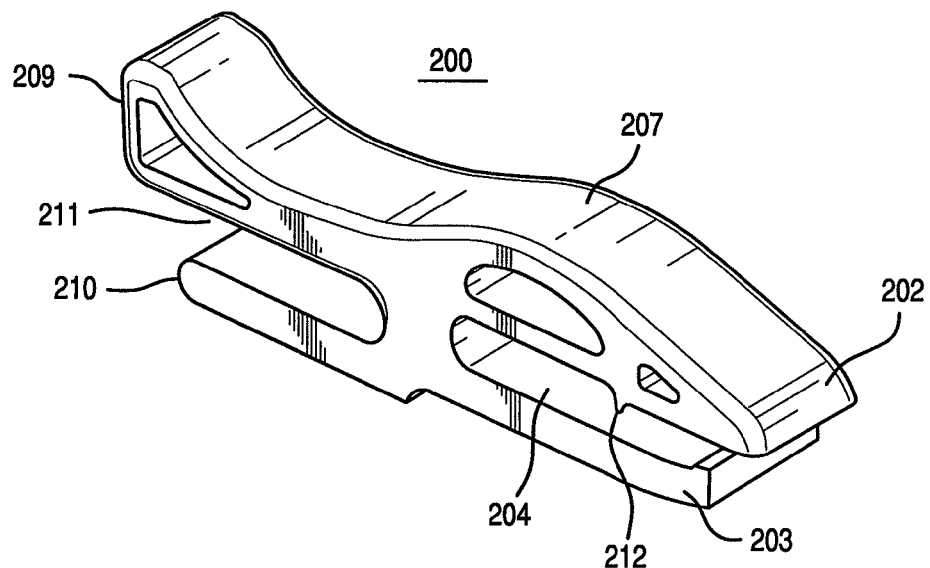
FIG. 20 illustrates a perspective view of the slidable sealing element.
Figure 21:
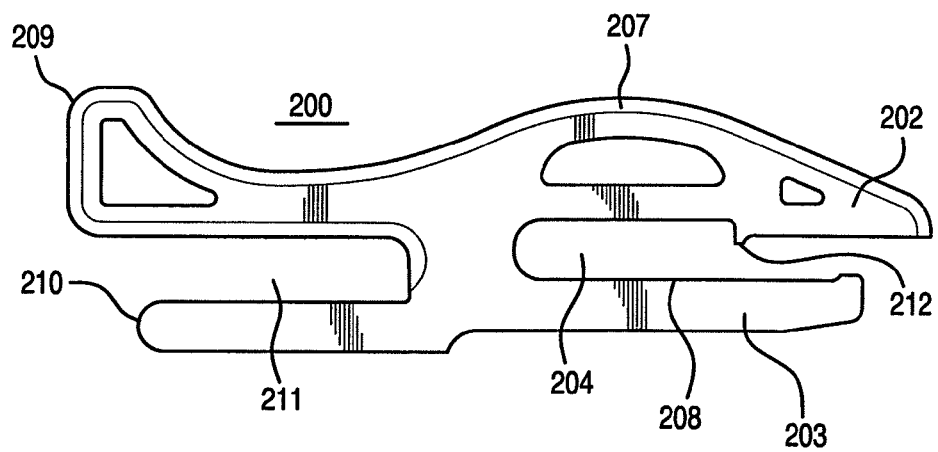
FIG. 21 illustrates a side view of the slidable sealing element.

The sealing element 200, also shown in FIGS. 20 and 21, has a proximal end and a distal end; the proximal end has at least one anterior prong 202 and at least one posterior prong 203, preferably the anterior prong has a greater thickness relative to the posterior prong when viewing a longitudinal cross section of the sealing element. The prongs are separated by a gap 204, which permits the slidable movement of said sealing element relative the cartridge. In operation, when the closure element is manually actuated the anterior prong slides over and across at least a portion of the device's substantially planar surface 205 in the region of the blood entry port; and the posterior prong slides under a portion of a face 206 of the cartridge opposite its substantially planar surface 205. Over and under are relative terms with respect to the cartridge. The sealing element may also include a dome-like shape 207 on the anterior prong while the posterior prong includes a substantially planar shape 208 when viewing the longitudinal cross section of said sealing element, as in FIG. 21. The gap 204 separating the prongs runs approximately half the length of said sealing element 200.

In operation, the anterior prong remains substantially rigid as this prong slides over and across the device at 205, while the posterior prong may flex as this prong slides under 205. The anterior prong may also be longer than the posterior prong so that a tip of the anterior prong extends beyond the tip of the posterior prong. The sealing element can also include, at the distal end, anterior prong 209 and posterior prong 210 separated by a gap 211 that runs approximately a third of the length of said sealing element. Optionally 209 may includes a fin-like shape, while 210 may have a substantially planar shape when viewing a longitudinal cross section of the sealing element. Preferably 209 has a tip that extends beyond 210. The sealing element is preferably made from a plastic material with mechanical properties and dimensions that permit the desired degree of flexing. Such materials include polyesters, ABS, acetal polymers and the like, that are suitable for injection molding.

The sealing element also can include a locking feature 212, which engages after the sealing element covers the blood entry port into a groove 213 in the base of the device. This ensures that the sealing element remains in the closed position throughout the assay procedure. Engagement of the sealing element in the closed position abuts it in an airtight manner to the region surrounding the blood entry port. Additionally, grooves and proud features may be molded into the sealing element and cartridge base to assure that when the sealing element is moved from the open to closed position, it tracks to the desired closed position completely covering the blood entry port. An additional locking feature may be included on prong 203 and the cartridge base.

The blood entry port 4 may be an orifice that is circular, as shown in FIG. 19, or oval and the diameter of the orifice is generally in the range 0.2-5 mm, preferably 1-2 mm, or having a perimeter of 1-15 mm for an oval. The region around the orifice may be selected to be hydrophobic or hydrophilic to control the drop-shape of the applied blood sample to promote entry into the entry port. Optionally, it may be a portion of an adhesive tape material 21 that is capable of forming an airtight seal with the sealing means.

One advantage of this sealing element is that it prevents blood being pushed beyond the capillary stop element 25 at the end of the blood holding chamber 34. The presence of a small amount of blood beyond the capillary stop is not significant for tests that measure bulk concentration of an analyte and thus do not depend on sample volume. However, for immunoassay applications where metering of the sample is generally advantageous the sealing element improves metering accuracy of the device and assures the assayed segment of sample is appropriately positioned with respect to the immunosensor, when the analyzer actuates the sample within the cartridge's conduits.

In operation, when blood is added to the cartridge it moves to the capillary stop. Thus sufficient blood for the assay is present when the region from the capillary stop to the blood entry port, i.e., the holding chamber, contains blood. During the process of filling the holding chamber some blood may remain above the plane of the orifice of the entry port. When the sealing element is moved from the opened to closed position, any blood that is above the entry port is sheared away without trapping additional blood in the act of closure, thus ensuring that blood does not move beyond 25. In a preferred embodiment, sealing element 200 is positioned within a few thousandths of an inch above the surface of the tape gasket 21 of FIG. 3. The entry port is sealed by the subsequent lowering of the surface of 200 to the adhesive tape gasket when it engages locking features 212 and 213. Once this seal is achieved it is essentially irreversible. Furthermore, since the tape is essentially incompressible and the orifice has a small diameter, any inadvertent pressure applied to the sealing element by the user will not cause the blood to move beyond the capillary stop.

While sealing element 200 and its attendant features are particularly advantageous for an immunoassay and DNA testing cartridges, they can also be used with cartridges that have sensors for other tests including sodium ion, glucose, activated clotting time and the like. It can be considered applicable to any cartridge with an immunosensor, electrochemical sensor, acoustic-wave sensor, optical sensor and the like.

Bubble-Free Blood Entry into Holding Chamber

A reliable means for introducing more than one drop of blood into the blood holding chamber without entraining bubbles has been developed. In certain cartridge embodiments that use several drops of blood, it is desirable that no bubbles form in the holding chamber as this can affect the assay. For example, in a coagulation assay, e.g., prothrombin time (PT), the cartridge needs to work with a few drops of blood from a fingerstick.

The blood-entry port can be designed to receive multiple drops of blood without successive drops causing trapped bubbles to form in the holding chamber 34 by treating the holding chamber with a Corona and/or a reagent cocktail. Surface 34 is first Corona treated to provide charged surface groups that will promote spreading of the aqueous printed cocktail.

The use of corona treatments on disposable medical devices is well known in the art. It is an effective way to increase the surface activity of virtually any material, e.g., plastics such as polyethylene, polypropylene, nylon, vinyl, PVC, and PET; metallized surfaces, foils, paper, and paperboard stock. This treatment makes them more receptive to inks, coatings, and adhesives. In practice the material being treated is exposed to an electrical discharge, or "corona." Oxygen molecules in the discharge area break into atoms and bond to molecules in the material being treated, resulting in a chemically activated surface. Suitable equipment for corona treatments is commercially available (e.g., Corotec Corp., Farmington, Conn.). The process variables include the amount of power required to treat the material, the material speed, the width, the number of sides to be treated, and the responsiveness of a particular material to corona treatment, which variables can be determined by a skilled operator. The typical place to install a corona treatment is in-line with the printing, coating, or laminating process. Another common installation is directly on a blown film or cast film extruder since fresh material is more receptive to corona treatment.

In general the cocktail may contain a water-soluble protein, an amino acid, a polyether, a polymer containing hydroxyl groups, a sugar or carbohydrate, a salt and optionally a dye molecule. One or more of each component can be used. In one embodiment the cocktail contains bovine serum albumin (BSA), glycine, methoxypolyethylene glycol, sucrose and optionally bromophenol blue to provide color that aids visualizing the printing process. A salt would be a component for an immunoassay. Typically, 1-20 uL of cocktail is printed onto the holding chamber before being assembled with its cover and allowed to air dry.

A preferred composition is given in Example 6 for a coagulation assay, in which the amount of each component printed in the sample holding chamber in the base (coating) is shown. The components are BSA, glycine, methoxypolyethylene glycol, sucrose and bromophenol blue. The sample holding chamber in the cartridge base is corona treated prior to printing. The cartridge cover need not be treated with either corona or cocktail although it may be advantageous for some assays. In a preferred embodiment there is no special treatment for the cover and no treatment around the blood entry orifice.

Printing is automated and based on a microdispensing system, including a camera and computer system to align components, as disclosed in U.S. Pat. No. 5,554,339, where the wafer chuck is replaced by a means for feeding the plastic cartridge bases to the dispensing head.

In operation, for efficient draw of blood into the holding chamber of small volumes (about 20 uL and less) it is desirable to have a high capillarity to clear the entry port of a first drop of blood so that a second can be added without spilling around the port due the first one being still partially there. The results for the corona (C) and reagent (R) treatment combinations are as follows:

1. C no, R no: No reliable blood draw is observed.
2. C no, R yes: Reagent does not coat holding chamber reliably. As for 1.
3. C yes, R no: Rapid blood draw is good for several weeks but can degrade with time.
4. C yes, R yes: Rapid blood draw is good and lasts for +6 months (a typical target for product shelf-life).

The reagent concentration must be low so that it works as desired, but does not interfere with the assay, e.g., components in blood that give rise to the coagulation cascade, as in PT, APTT and ACT assays. One skilled in the art will not need unreasonable experimentation here, i.e., freshly made cartridges with processes 3 and 4 should have the same assay results. The actual concentrations will depend on the design of the cartridge, dimensions, plastics etc.

Electrochemical Immunosensor with Reduced Background

The signal-to-noise ratio is a well known factor in any measurement. Here, we provide a means for reducing the noise (or background signal) in an amperometric immunoassay. It has been discovered that the immunosensor exhibits reduced non-Faradaic (background or charging current) signal, by adding certain porous layers interposed between the electrode and the antibody layer. This type of assay relies on measuring currents in the nanoampere range with comparatively low concentrations of electroactive species (e.g., p-aminophenol), thus the background current can be a significant portion of the measured signal.

It has been discovered that an intervening polyvinyl alcohol (PVA) layer of about 0.5-5.0 micron thickness (preferably 0.6-1.0 micron) placed between the electrode and the antibody reagent layer significantly attenuates the background component. An advantage of PVA as the background-reducing layer is that noise is reduced without appreciably affecting the Faradaic component of the signal. While the PVA layer reduces the diffusion coefficient of small molecules by about 50% it has been found that it does not change the current at the coated electrodes, for two reasons. First, with PVA layers of about 1 micron thickness, the detected electroactive species is present in a diffusion layer of at least ten times that thickness, so there is little decrease in transport due to the PVA layer. Second, a steady-state current is measured in the immunosensor which is effectively independent of the transport rate and electrode kinetics, but is a function of the enzymatic rate of production of the detectable species, such as p-aminophenol generated from p-aminophenol phosphate by the enzyme alkaline phosphatase (attached to the second antibody).

Wafer-level microfabrication of a preferred embodiment of the immunosensor is as follows. The base electrode (94 of FIG. 9) consists of a square array of 7 um gold disks on 15 um centers. The array covers a circular region approximately 600 um in diameter, and is achieved by photo-patterning a thin layer of polyimide of thickness 0.35 um over a substrate made from a series of layers comprising Si/SiO2/TiW/Au. The array of 7 um microelectrodes affords high collection efficiency of electroactive species with a reduced contribution from any electrochemical background current associated with the capacitance of the exposed metal. The inclusion of a PVA layer over the metal significantly enhances the reduction of background currents.

The porous PVA layer is prepared by spin-coating an aqueous mixture of PVA plus a stilbizonium photoactive, cross-linking agent over the microelectrodes on the wafer. The spin-coating mixture optionally includes bovine serum albumin (BSA). It is then photo-patterned to cover only the region above and around the arrays and preferably has a thickness of about 0.6 um.

The improved background screening properties of the PVA layer were established by including alkaline phosphatase (ALP) into the patterned layer to assess collection efficiency and by comparing the background and p-aminophenol currents in solutions containing ALP. The PVA layer was associated with a reduction in background current of about a factor of three, without any significant attenuation of the p-aminophenol signal.

Without being bound to theory, suppression of the background current is likely to involve a degree of permselectivity towards p-aminophenol over electrochemical contaminants and other species that adsorb at the electrode surface which modify the double layer capacitance. Alternatively, the layer may have an effect on the electrode surface that preferentially reduces the rate of electrochemically irreversible (background) reactions, while affecting relatively reversible reactions, e.g., p-aminophenol, to a lesser degree. Also, the absorbent nature of the PVA layer may aid in maintaining continuity (conductivity) during an amperometric analysis. Failure to maintain conductivity may result in a drifting potential that would contribute to background noise.

Immuno-Reference Sensor

The general concept of differential measurement is known in the electrochemical and sensing arts. A novel means for reducing interfering signals in an electrochemical immunosensing systems is now described. However, while it is described for pairs of amperometric electrochemical sensors it is of equal utility in other electrochemical sensing systems including potentiometric sensors, field effect transistor sensors and conductimetric sensors. It is also applicable to optical sensors, e.g., evanescent wave sensors and optical wave guides, and also other types of sensing including acoustic wave and thermometric sensing and the like. Ideally, the signal from an immunosensor (IS) is derived solely from the formation of a sandwich between an immobilized antibody (the analyte) and a second antibody that is labeled, wherein the label (e.g., an enzyme) reacts with a substrate to form a detectable product (1).

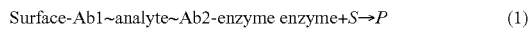

Surface-Ab1~analyte~Ab2-enzyme enzyme+$S \rightarrow P$  (1)

It is known that some of the second antibody can bind non-specifically to the surface (2, 3) and might not be washed away completely from the region of the immunosensor (up to approx. 100 microns away) during the washing step, giving rise to a portion of the total detected product that is not a function of the surface-Ab1~analyte binding reacting; that is, an interfering signal.

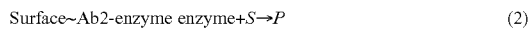

Surface~Ab2-enzyme enzyme+$S \rightarrow P$  (2)

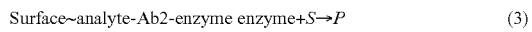

Surface~analyte-Ab2-enzyme enzyme+$S \rightarrow P$  (3)

A second immunosensor can be placed in the cartridge that acts as an immuno-reference sensor (IRS) and gives the same (or a predictably related) degree of non-specific binding as occurs on the primary immunosensor. Interference can be reduced by subtracting the signal of this immuno-reference sensor from that of the immunosensor, i.e., the non-specific binding component of the signal is removed, improving the performance of the assay (4).

Corrected signal=IS−IRS  (4)

The immuno-reference sensor is preferably the same in all significant respects (e.g., dimensions, porous screening layer, latex particle coating, and metal electrode composition) as the immunosensor except that the capture antibody for the analyte (for instance, cTnI) is replaced by an antibody to a plasma protein that naturally occurs in samples (both normal and pathological) at a high concentration. The immunosensor and reference immunosensor may be fabricated as adjacent structures 94 and 96, respectively, on a silicon chip. While the preferred embodiment is described for a troponin I assay, this structure is also useful for other cardiac marker assays including troponin T, creatine kinase MB, procalcitonin, BNP, proBNP, myoglobin and the like, plus other sandwich assays used in clinical diagnostics.

Examples of suitable antibodies that bind to plasma proteins include antibodies to human serum albumin, fibrinogen and IgG fc region, with albumin being preferred. However, any native protein or blood component that occurs at a concentration of greater than about 100 ng/mL can be used if an appropriate antibody is available. The main requirement of the protein is being present in sufficient amounts to coat the sensor quickly compared to the time needed to perform the analyte assay. In a preferred embodiment, the protein is present in a blood sample at a concentration sufficient to bind more than 50% of the available antibody on the reference immunosensor within about 100 seconds of contacting a blood sample. In general the second immobilized antibody has an affinity constant of about $1 \times 10(-7)$ to about $1 \times 10(-15)$M. For example, an antibody to albumin having an affinity constant of about $1 \times 10(-10)$ M is preferred, due to the high molar concentration of albumin in blood samples, which is about $1 \times 10(-4)$ M.

It has been found that providing a surface that is covered by native albumin derived from the sample significantly reduces the binding of other proteins and cellular materials which may be present. This method is generally superior to prior art immunoassays that use conventional blocking agents to minimize non-specific binding. Because these agents must typically be dried down and remain stable for months or years before use, during which time they may degrade, creating a stickier surface than desired and resulting in non-specific binding that rises with age. In contrast the method described here provides a fresh surface at the time of use.

An immunosensor for cardiac troponin I (cTnI) with a reference-immunosensor for performing differential measurement to reduce the effect of non-specific binding is described next. Carboxylate-modified latex microparticles (supplied by Bangs Laboratories Inc. or Seradyn Microparticles Inc.) coated with anti-cTnI and anti-HSA are both prepared by the same method. The particles are first buffer exchanged by centrifugation, followed by addition of the antibody, which is allowed to passively adsorb onto the particles. The carboxyl groups on the particles are then activated with EDAC in MES buffer at pH 6.2, to form amide bonds to the antibodies. Any bead aggregates are removed by centrifugation and the finished beads are stored frozen.

It was found that for the anti-human serum albumin (HSA) antibody, saturation coverage of the latex beads results in about a 7% increase in bead mass. Coated beads were prepared using covalent attachment from a mixture comprising 7 mg of anti-HSA and 100 mg of beads. Using this preparation a droplet of about 0.4 mL, comprising about 1% solids in deionized water, was microdispensed (using the method and apparatus of U.S. Pat. No. 5,554,339, incorporated here by reference) onto a photo-patterned porous polyvinyl alcohol permselective layer covering sensor 96, and allowed to dry. The dried particles adhered to the porous layer and substantially prevented their dissolution in the blood sample or the washing fluid.

For the troponin antibody, saturation coverage of the latex bead surface resulted in a mass increase in the beads of about 10%. Thus by adding 10 mg of anti-TnI to 100 mg of beads along with the coupling reagent, saturation coverage was achieved. These beads were then microdispensed onto sensor 94.

In an another embodiment, immunosensor 94 is coated with beads having both a plasma protein antibody, e.g., anti-HSA, and the analyte antibody, e.g., anti-cTnI. Latex beads made with the about 2 mg or less of anti-HSA per 100 mg of beads and then saturation-coated with anti-cTnI provide superior non-specific binding properties at the immunosensor. It has been found that the slope (signal versus analyte concentration) of the troponin assay is not materially affected because there is sufficient anti-cTnI on the bead to capture the available analyte (antigen). By determining the bead saturation concentration for different antibodies, and the slope of an immunosensor having beads with only the antibody to the target analyte, appropriate ratios of antibody combinations can be determined for beads having antibodies to both a given analyte and a plasma protein.

An important aspect of immunosensors having a reference immunosensor is the "humanizing" of the surface created by a layer of plasma protein, preferably the HSA/anti-HSA combination. This appears to make the beads less prone to non-specific binding of the antibody-enzyme conjugate. It also seems to reduce bead variability. Without being bound by theory, it appears that as the sensors are covered by the sample they are rapidly coated with native albumin due to the anti-HSA surface. This gives superior results compared to conventional blocking materials which are dried down in manufacturing and re-hydrated; typically after a long period in storage. Another advantage to "humanizing" the sensor surface is that it provides an extra mode of resistance to human anti-mouse antibodies (HAMA) and other heterophile antibody interferences. The effects of HAMA on immunoassays are well known.

Another use of the immuno-reference sensor of the invention is to monitor the wash efficiency obtained during the analytical cycle. As stated above, one source of background noise is the small amount of enzyme conjugate still in solution, or non-specifically absorbed on the sensor and not removed by the washing step. This aspect of the invention relates to performing an efficient washing step using a small volume of washing fluid, by introducing air segments as mentioned in Example 2.

In operation of the preferred embodiment, which is an amperometric electrochemical system, the currents associated with oxidation of p-aminophenol at immunosensor 94 and immuno-reference sensor 96 arising from the activity of ALP, are recorded by the analyzer. The potentials at the immunosensor and immuno-reference sensor are poised at the same value with respect to a silver-silver chloride reference electrode. To remove the effect of interference, the analyzer subtracts the signal of the immuno-reference sensor from that of the immunosensor according to equation (4). Where there is a characteristic constant offset between the two sensors, this also is subtracted. It will be recognized that it is not necessary for the immuno-reference sensor to have all the same non-specific properties as the immunosensor, only that it be consistently proportional in both the wash and non-specific binding parts of the assay. An algorithm embedded in the analyzer can account for any other essentially constant, difference between the two sensors.

Use of a differential combination of immunosensor and immuno-reference sensor, rather than an immunosensor alone, provides the following improvement to the assay. In a preferred embodiment the cartridge design provides dry reagent that yields about 4-5 billion enzyme conjugate molecules dissolved into about a 10 uL blood sample. At the end of the binding and wash steps the number of enzyme molecules at the sensor is about 70,000. In experiments with the preferred embodiment there were, on average, about 200,000 (+/−about 150,000) enzyme molecules on the immunosensor and the reference immunosensor as non-specifically bound background. Using a differential measurement with the immuno-reference sensor, about 65% of the uncertainty was removed, significantly improving the performance of the assay. While other embodiments may have other degrees of improvement, the basis for the overall improvement in assay performance remains.

An additional use of this immuno-reference sensor is to detect anomalous sample conditions, such as improperly anti-coagulated samples which deposit material throughout the conduits and cause increased currents to be measured at both the immunosensor and the immuno-reference sensor. This effect is associated with both non-specifically adsorbed enzyme and enzyme remaining in the thin layer of wash fluid over the sensor during the measurement step.

Another use of the immuno-reference sensor is to correct signals for washing efficiency. In certain embodiments the level of signal at an immunosensor depends on the extent of washing. For example, longer washing with more fluid/air segment transitions can give a lower signal level due to a portion of the specifically bound conjugate being washed away. While this may be a relatively small effect, e.g., less than 5%, correction can improve the overall performance of the assay. Correction may be achieved based on the relative signals at the sensors, or in conjunction with a conductivity sensor located in the conduit adjacent to the sensors, acting as a sensor for detecting and counting the number of air segment/fluid transitions. This provides the input for an algorithmic correction means embedded in the analyzer.

In another embodiment of the reference immunosensor with an endogenous protein, e.g., HSA, it is possible to achieve the same goal by having an immuno-reference sensor coated with antibody to an exogenous protein, e.g., bovine serum albumin (BSA). In this case the step of dissolving a portion of the BSA in the sample, provided as an additional reagent, prior to contacting the sensors is needed. This dissolution step can be done with BSA as a dry reagent in the sample holding chamber of the cartridge, or in an external collection device, e.g., a BSA-coated syringe. This approach offers certain advantages, for example the protein may be selected for surface charge, specific surface groups, degree of glycosylation and the like. These properties may not necessarily be present in the available selection of endogenous proteins.

Immunosensor with Improved Precision

An electrochemical immunosensor of the type described here can exhibit a bias between whole-blood versus plasma. Historically, immunoassays for markers such as troponin and the like are measured and reported as plasma or serum values. When these immunosensors are used for analysis of whole-blood, either a correction factor or a means for eliminating the bias needs to be employed. It has been found that two aspects of this bias can be eliminated: (i) the bias in whole-blood electrochemical immunoassays associated with components of the buffy coat (which consists of white blood cells and platelets), and (ii) the bias associated with hematocrit variations between samples.

The buffy coat is a layer of leukocytes and platelets that forms above the erythrocytes when blood is centrifuged. It has been observed that a white cell (or leukocyte) interference occurs on immunosensors having beads coated with an analyte antibody, e.g., troponin antibody. Control experiments showed that this positive bias is absent in plasma samples and in blood samples where the buffy coat has been removed. Without being bound by theory, it appears that leukocytes are able to stick to the immunosensor and promote non-specific binding of the enzyme-labeled antibodies, which remain bound even after a washing step. It has been found that this bias can be partially eliminated by adding a small amount of an antibody to human serum albumin during bead preparation. When a sample contacts the modified beads, albumin from the sample rapidly coats the beads as described above. Once they are coated with a layer of native albumin the leukocytes do not recognize the beads as an opsonized surface, resulting in the observed effect of limiting the leukocytes' ability to cause the bias.

Another solution to the leukocyte interference problem has also been discovered. This bias can be eliminated by increasing the salt concentration of the blood sample from a normal sodium ion concentration of about 140 mM to above about 200 mM, preferably to about 230 mM. For convenience, the salt's effective concentration is expressed as the sodium ion concentration. FIG. 22 is a graph of the difference in net current at the immunosensor versus added NaCl concentration. In a preferred embodiment, sufficient salt is added to the blood-holding chamber of the cartridge in a dried down form able to dissolve in the sample prior to the measurement step. Because the holding chamber has a volume of about 10 uL in the preferred cartridge design, this requires about 60 ug of NaCl. Without being bound by theory, a mechanism that accounts for reduced interference may be that the salt causes osmotic shrinkage of the leukocytes, since this is an established phenomenon with erythrocytes. This interpretation is consistent with the leukocytes' impaired ability to interact with the immunosensor.

Suitable salts are not limited to NaCl, for example KCl, MgCl2, CaCl2, LiCl, NaNO3, Na2SO4 can be used, as well as common buffer salts, e.g., Tris, MES, phosphate and HEPES. The type of salt and effective concentration range to obviate the buffy coat interference effect can be determined by routine experimentation. Other alternatives that have a similar effect include sugars, DEAE dextran and lactitol. These materials can also be used as the matrix for printing the salt into the cartridge.

In a preferred embodiment salt is added to the sample by coating the wall of the sample holding chamber with a mixture of NaCl, lactitol and DEAE dextran at pH 7.4 using Tris at about 5% total solids. Gelatin, cellulose and PVA can also be used as the support matrix, but the dissolution rate is not quite as fast as the lactitol and DEAE mixture.

It has been found that the addition of salt before the assay can be used advantageously in combination with the HSA-antibody coated beads on the immunosensor.

In addition to salts, other reagents can improve whole-blood precision in an immunoassay. These reagents should be presented to the blood sample in a way that promotes rapid dissolution. Support matrices including cellulose, polyvinyl alcohol and gelatin (or mixtures thereof) that are coated on to the wall of the blood-holding chamber (or another conduit) promote rapid dissolution, e.g., greater than 90% complete in less than 15 seconds.

Other optional additives may be included into the cartridge or used in conjunction with the assay. The anticoagulant heparin can be added to improve performance in cases where the sample was not collected in a heparinized tube or was not properly mixed in a heparinized tube. Enough heparin is added so that fresh unheparinized blood will remain uncoagulated during the assay cycle of the cartridge, typically in the range of 2-20 minutes. Goat and mouse IgG can by added to combat heterophile antibody problems well known in the immunoassay art. Proclin, DEAE dextran, Tris buffer and lactitol can be added as reagent stabilizers. Tween 20 can be added to reduce binding of proteins to the plastic, which is the preferred material for the cartridge. It also allows the reagents to coat the plastic surface more evenly and acts as an impurity that minimizes the crystallization of sugars, such as lactitol, so that they remain a glass. Sodium azide may be added to inhibit bacterial growth.

Immunosensor with Reduced Hematocrit Interference

Sample hematocrit values may vary widely between immunoassays performed on whole-blood and this can affect the results. A way to eliminate this effect has been discovered. Experiments showed that when the blood sample is placed over the immunosensor in the cartridge, the reagents that form the immunocomplex dissolve into the plasma fraction only, not into the cells, which are predominantly erythrocytes. Erythrocytes typically occupy about 40% of a blood sample, though this can vary widely between patients. The percentage of the blood sample volume occupied by these cells is called the hematocrit value. For a given volume of blood, the higher the hematocrit value the less plasma volume is available for a given amount of reagent to dissolve in; thus, the effective reagent concentration is higher. Therefore, it was observed that the signal generated in the assay increases with increasing hematocrit. This effect can be corrected for by measuring the hematocrit of the sample during the assay. The analyte concentration can then be reported so as to agree with typical laboratory values obtained from spun samples, i.e., serum or plasma samples where hematocrit equals zero.

We have found that measurement of the bulk conductivity of the sample with (or without) the dissolved reagents gives an adequate estimate of the hematocrit. It is known that the hematocrit is an inverse function of conductivity, assuming a normal concentration of current-carrying ions in the sample. In one embodiment standard curves are created using samples with independently determined analyte concentrations and hematocrit values. One skilled in the art will understand that an algorithm can be developed and embedded into the analyzer and used for real samples, whereby the conductivity measured at an adjacent sensor in the cartridge is used to estimate hematocrit and correct the signal from the immunosensor. For example, the algorithm may simply subtract a percentage of the signal per hematocrit unit in order to correct the result to a hematocrit of zero, i.e., plasma.

Immunosensor Correction for Buffy Coat and Hematocrit

The embodiments described above provide means for the individual elimination of the buffy coat interference and variable hematocrit values in electrochemical immunoassays performed on whole-blood samples. It is however desirable to deal with both interferences in the same sample and at the same sensor. The following method assures that the addition of salt to the sample to eliminate the buffy coat interference does not affect the hematocrit measurement, which is based on a conductivity measurement. Those skilled in the art will recognize that adding salt to a blood sample with an otherwise normal concentration of ions will increase its conductivity, thus giving an inaccurately low value of hematocrit. The present embodiment minimizes this problem. It has been found that when adding salt to the blood holding chamber, the plot of signal versus hematocrit is non-linear because the final plasma volume and resulting conjugate concentration depend on both the initial hematocrit value and the amount of erythrocyte shrinkage resulting from adding a fixed amount of salt. It has been found that a plot of signal versus hematocrit provides a parabolic curve if the data are normalized to plasma, i.e., if signal in plasma is unity, then the curve is the same regardless of the analyte concentration, e.g., [cTnI]. This is also true if the signal is plotted versus sample conductivity.

The most facile means for correcting data arising from an assay using a salt print is as follows; (i) measure the net signal current for the assay (corrected for the reference immunosensor current) using the method described above; equation (4), (ii) measure the sample conductivity after dissolution of the holding chamber salt print, i.e., make the measurement of conductivity during capture/mixing, (iii) from the measured sample conductivity of step 2, calculate the value of the Plasma Normalization Current Function (PNCF)=$c1*Cond^2+c2*Cond+c3$ (PNCF=unity for plasma), and (iv) divide the net current from step 1, by the correction factor calculated in step 3 to yield the "plasma [analyte]".

Regarding the parabolic curve, it has been found that as hematocrit increases from zero to about 30 percent, the PNCF increases from 1.0 to about 1.3 and as the hematocrit further increases from about 30 to about 60, the PNCF decreases back to a value of about 1.0. The advantage of using this method is that the algorithm for the correction no longer involves discrete estimation of the hematocrit of the sample. Here, the salt addition can be generalized to increased ionic strength or osmolarity in minimizing the buffy coat interference.

While this is the preferred method for the preferred immunosensor and cartridge elements described above, those skilled in the art will recognize that other component combinations, particularly for other analytes may require re-optimization of the PNCF algorithm using different constants and the like.

A cartridge of the present invention has the advantage that the sample and a second fluid can contact the sensor array at different times during an assay sequence. The sample and second fluid may also be independently amended with other reagents or compounds present initially as dry coatings within the respective conduits. Controlled motion of the liquids within the cartridge further permits more than one substance to be amended into each liquid whenever the sample or fluid is moved to a new region of the conduit. In this way, provision is made for multiple amendments to each fluid, greatly extending the complexity of automated assays that can be performed, and therefore enhancing the utility of the present invention.

In a disposable cartridge, the amount of liquid contained is preferably kept small to minimize cost and size. Therefore, in the present invention, segments within the conduits are also used to assist in cleaning and rinsing the conduits by passing the air-liquid interface of a segment over the sensor array or other region to be rinsed at least once. It has been found that more efficient rinsing, using less fluid, is achieved by this method compared to continuous rinsing by a larger volume of fluid.

Restrictions within the conduits serve several purposes in the present invention. A capillary stop located between the sample chamber and first conduit is used to prevent displacement of the sample in the holding chamber until sufficient pressure is applied to overcome the resistance of the capillary stop. A restriction within the second conduit is used to divert wash fluid along an alternative pathway towards the waste chamber when the fluid reaches the constriction. Small holes in the gasket, together with a hydrophobic coating, are provided to prevent flow from the first conduit to the second conduit until sufficient pressure is applied. Features that control the flow of liquids within and between the conduits of the present invention are herein collectively termed "valves."

One embodiment of the invention, therefore, provides a single-use cartridge with a sample-holding chamber connected to a first conduit which contains an analyte sensor or array of analyte sensors. A second conduit, partly containing a fluid, is connected to the first conduit and air segments can be introduced into the fluid in the second conduit in order to segment it. Pump means are provided to displace the sample within the first conduit, and displaces fluid from the second conduit into the first conduit. Thus, the sensor or sensors can be contacted first by a sample and then by a second fluid.

A second embodiment of the cartridge includes a closeable valve located between the first conduit and a waste chamber. This embodiment permits displacement of the fluid from the second conduit into the first conduit using only a single pump means connected to the first conduit. This embodiment further permits efficient washing of the conduits of the cartridge of the present invention, which is an important feature of a small single-use cartridge. In operation, the sample is displaced to contact the sensors, and is then displaced through the closeable valve into the waste chamber. Upon wetting, the closeable valve seals the opening to the waste chamber, providing an airtight seal that allows fluid in the second conduit to be drawn into contact with the sensors using only the pump means connected to the first conduit. In this embodiment, the closeable valve permits the fluid to be displaced in this manner and prevents air from entering the first conduit from the waste chamber.

In another embodiment, both a closeable valve and means for introducing segments into the conduit are provided. This embodiment has many advantages, among which is the ability to reciprocate a segmented fluid over the sensor or array of sensors. Thus a first segment or set of segments is used to rinse a sensor, and then a fresh segment replaces it for taking measurements. Only one pump means (that connected to the first conduit) is required.

In a fourth embodiment analyte measurements are performed in a thin-film of liquid coating an analyte sensor. Such thin-film determinations are preferably performed amperometrically. This cartridge differs from the foregoing embodiments in having both a closeable valve that is sealed when the sample is expelled through the valve, and an air vent within the conduits that permits at least one air segment to be subsequently introduced into the measuring fluid, thereby increasing the efficiency with which the sample is rinsed from the sensor, and further permitting removal of substantially all the liquid from the sensor prior to measurement, and still further permitting segments of fresh liquid to be brought across the sensor to permit sequential, repetitive measurements for improved accuracy and internal checks of reproducibility.

The analysis scheme for the detection of low concentrations of immunoactive analyte relies on the formation of an enzyme labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce about nine thousand detectable molecules per minute, providing several orders of magnitude improvement in the detectability of the analyte compared to schemes in which an electroactive species is attached to the antibody in place of alkaline phosphatase.

In immunosensor embodiments, it is advantageous to contact the sensor first with a sample and then with a wash fluid prior to recording a response from the sensor. In specific embodiments, the sample is amended with an antibody-enzyme conjugate that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides either a current from a redox reaction at the electrode when a suitable potential is applied (amperometric operation). Alternatively, if the electroactive species is an ion, it can be measured potentiometrically. In amperometric measurements the potential may either be fixed during the measurement, or varied according to a predetermined waveform. For example, a triangular wave can be used to sweep the potential between limits, as is used in the well-known technique of cyclic voltammetry. Alternatively, digital techniques such as square waves can be used to improve sensitivity in detection of the electroactive species adjacent to the electrode. From the current or voltage measurement, the amount or presence of the analyte in the sample is calculated. These and other analytical electrochemical methods are well known in the art.

In embodiments in which the cartridge comprises an immunosensor, the immunosensor is advantageously microfabricated from a base sensor of an unreactive metal such as gold, platinum or iridium, and a porous permselective layer which is overlaid with a bioactive layer attached to a microparticle, for example latex particles. The microparticles are dispensed onto the porous layer covering the electrode surface, forming an adhered, porous bioactive layer. The bioactive layer has the property of binding specifically to the analyte of interest, or of manifesting a detectable change when the analyte is present, and is most preferably an immobilized antibody directed against the analyte.

In operation, therefore, one goal of the present invention is to provide an immunosensor cartridge that is preferably operated in a basic sense as follows. (However, the invention is not restricted to embodiments comprising an immunosensor, but includes any ligand-receptor interaction, including complimentary strands of DNA and RNA, biotin-avidin and the like.) An unmetered amount of a preferably biological sample is placed into the sample chamber of the cartridge, and the cartridge is placed into a reading apparatus. A metered portion of the sample is amended with at least one antibody-enzyme conjugate, and is then contacted with the immunosensor. A second fluid, which contains an electroinactive substrate for the enzyme, is used to rinse the immunosensor substantially free of unbound antibody-enzyme conjugate, and the electrical response of the immunosensor electrode is recorded and analyzed for the presence, or amount of, the analyte of interest. The cartridge may contain a plurality of immunosensors and reagents.

Signal Corrections

The calculation and correction methods can best be understood by referring to FIGS. 23 and 24. A preferred embodiment is described with reference to a TnI cartridge cycle which involves amperometric measurements with two sensors, the cTnI sensor (amp0, ParamAct) which bears the immunoassay reagent capable of specific binding of analyte to the sensor surface, and a reference sensor (amp0, ParamRef) bearing an immunoassay reagent capable of specific binding of human serum albumin (HSA). The reference sensor becomes coated with HSA upon introduction of the sample and is used to assess and correct for non-specific binding of signal-generating reagent (conjugate). The net current is calculated according to equation 5 (re-number equations below starting at 5) below; where the coefficient $c0$ is an optional manufacturing cartridge lot-specific value determined as the bias between amp0 and amp1 for un-spiked whole-blood and plasma, i.e., any bias in the absence of analyte.

$$iNet = ParamAct - ParamRef - c0 \text{(nanoamperes)} \quad\quad 5$$

Various options exist for managing any temperature effect on an immunoassay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value. In another embodiment, where a battery-powered analyzer is used and it is generally desirable to conserve battery life, it may be desirable to heat only the capture location of the assay device or cartridge. Here the ambient temperature will have an effect on the cooling of the sample if it enters regions adjacent to the capture location. In this example, the analyte capture and signal generation steps may have small temperature dependencies and so it is desirable that the net current is corrected to an ambient temperature (ATemp), e.g., 23° C., for example in accordance with equation 6. The value of the (per degree) coefficient $c1$ is generally not specific to a given lot of manufactured cartridges, but can be generalized to a given cartridge manufacturing process. It generally has a relatively small value, e.g., 1 to 3%. One skilled in the art will recognize that this can be determined from temperature-dependence experiments.

$$iTCorr = iNet*(1+c1*(ATemp-TempC)) \quad\quad 6$$

It has been found that the amount of antigen captured and labeled on the sensor surface is dependent on the conductivity of the blood. Several phenomena described below contribute to this aspect of the assay method. As described below, upon introduction to the cartridge the sample is treated with NaCl and other agents included in the sample holding chamber, to reduce interferences related to white blood cells and other components that can cause elevated readings in some samples. The hypertonicity induced by the introduction of NaCl is observed to cause shrinkage of cells, red blood cells representing the greatest mass fraction. As stated below, the amount of shrinkage is dependent on the plasma concentration of added NaCl, which is in turn dependent on the original hematocrit (Hct) of the sample. Thus, the final hematocrit of the sample depends on the original hematocrit and the amount of salt added. The conductivity of the sample after shrinkage depends on the final hematocrit and the final ionic strength.

The capacity for capture of signal generating reagents depends on the analyte concentration and the conjugate concentration, both of which become modified upon introduction of NaCl by virtue of the cell shrinkage. In the absence of added NaCl, the signal generation for a particular TnI sample will increase (approximately linearly) with increasing Hct. However, when addition of NaCl is factored into the equation, this linearity is transformed into quadratic behavior: as Hct increases from 0, signal generation increases due to increasing conjugate concentration. However, as the Hct increases further, signal generation begins to decrease because the added NaCl causes increasing cell shrinkage and a corresponding decrease in conjugate and analyte concentration. This is because the TnI (released from heart muscle) is restricted to the plasma portion of the blood sample. As the conductivity is dependent on both the Hct and the ionic strength, it has been found that the net signal generation is approximated by a quadratic function of the conductivity measured after cell shrinkage takes place. For this reason, it is desirable that the analytical signal is subjected to a conductivity correction that corrects the net current to the value expected in plasma (Hct=0).

The conductivity correction function can be determined experimentally, where a whole blood sample is spiked with a known amount of TnI, and manipulated through centrifugation and alteration of the plasma fraction so as to yield an array of standardized samples having the same plasma concentration of analyte but Hct varying from 0 to approximately 65 percent. Performing an immunoassay of these samples in the cartridges affords collection of a set of signals as a function of conductivity. Normalization of this function, so that plasma is associated with a signal generation factor of unity, affords the conductivity correction function. This may take one of several mathematical forms, including four point logistical functions and the quadratic form shown in equation 7. In this example, ResHct is the resistance at the hematocrit (conductivity) sensor after the sample has been amended by the reagent.

$$fCond = c2*ResHct^2 + c3*ResHct + c4 \qquad 7$$

One skilled in the art will recognize that the actual coefficients in Equation 7 will depend on the reagent components and have some sensitivity to the means by which the immunoassay is carried out, e.g., the capture time. In one embodiment, the value of fCond is limited by equations 8 and 9. In equation 8, if the measured conductivity is below a value expected for a Hct value of for example 15 percent, then the sample is treated as a plasma sample and the correction factor is set to 5. Equation 9 says that if the sample is clearly not a plasma sample and the correction factor is smaller than 0.8, then limit the correction to 0.8. Note that it is straightforward to find that the maximum value of fCond occurs when ResHct=$-\frac{1}{2}*(c3/c2)$.

$$\text{If ResHct<MaxPlasmaCond set fCond=1} \qquad 8$$

$$\text{If ResHct>MaxPlasmaCond and fCond<MinfCond,} \\ \text{set fCond=MinfCond} \qquad 9$$

Where MaxPlasmaCond=1050 and MinfCond=0.8

The correction factor as determined via equations 7-9 is applied as defined in equation 10.

$$iCorr = iTCorr/fCond \qquad 10$$

The analyte concentration is then calculated, for example by one of equations 11-13 below. In one embodiment, the cartridge is provided with a barcode with factory set information including the equations to be used and the required test coefficients. The analyzer, into which the cartridge is inserted to run the test, is thus equipped with a barcode reader. A selection of equations may be embedded in the software of the analyzer. For example, the coefficients for the cartridge may differ, where different lots of cartridges are manufactured, each lot having slightly different factory-determined characteristics. In any event, the coefficients for the cartridge, from whichever manufacturing lot the cartridge is drawn, are conveyed to the analyzer for use in one or more of the equations, for that particular cartridge test. For example, if a given digit of the cartridge barcode is set to 1, the analyzer may set c6 to zero, whereas other digits may code for different coefficients or select a kinetic model to be used, e.g., an immunoassay model formulated by analogy to the well-known Michaelis-Menton enzyme kinetics, as in equation 11.

$$[cTnI](\text{ng/mL}) = c6*i\text{Corr}/(c5*c6 - i\text{Corr}) \qquad 11$$

$$[cTnI](\text{ng/mL}) = c7*i\text{Corr}^2 + c7*c8*i\text{Corr} \qquad 12$$

$$\begin{aligned}[cTnI](\text{ng/mL}) &= c6*i\text{Corr}/(c5*c6 - i\text{Corr}) + \\ &\quad c7*i\text{Corr}^2 + c7*c8*i\text{Corr} \\ &= c6*i\text{Corr}/(c5*c6 - i\text{Corr}) + \\ &\quad c7*i\text{Corr}^2 + Linear*i\text{Corr}\end{aligned} \qquad 13$$

In the event that the Michaelis-Menton model is employed, an additional limit may be imposed, for example as defined by equation 12.

$$\text{If } i\text{Corr} > 0.9*c5*c6, \text{ set } i\text{Corr} = 0.9*c5*c6 \qquad 14$$

In addition, as a practical matter in reporting an analyte value to the user, (typically a physician by means of a display screen on the analyzer), in a given range from zero to an upper maximum value, one skilled in the art will recognize that the maximum theoretical current that can be observed is equal to the product c5*c6. Thus it is desirable that iCorr is limited to 90% of this value (equation 14) in order to avoid approaching the point of discontinuity inherent in the Michaelis-Menton term, i.e., when iCorr=c5*c6. As a result, the reported value can be limited to a given range. In the troponin cartridge example, the reported [cTnI] value is thus restricted to the range equal to or greater than zero and less than or equal to 50 ng/mL.

Cartridge Construction

Figure 2:
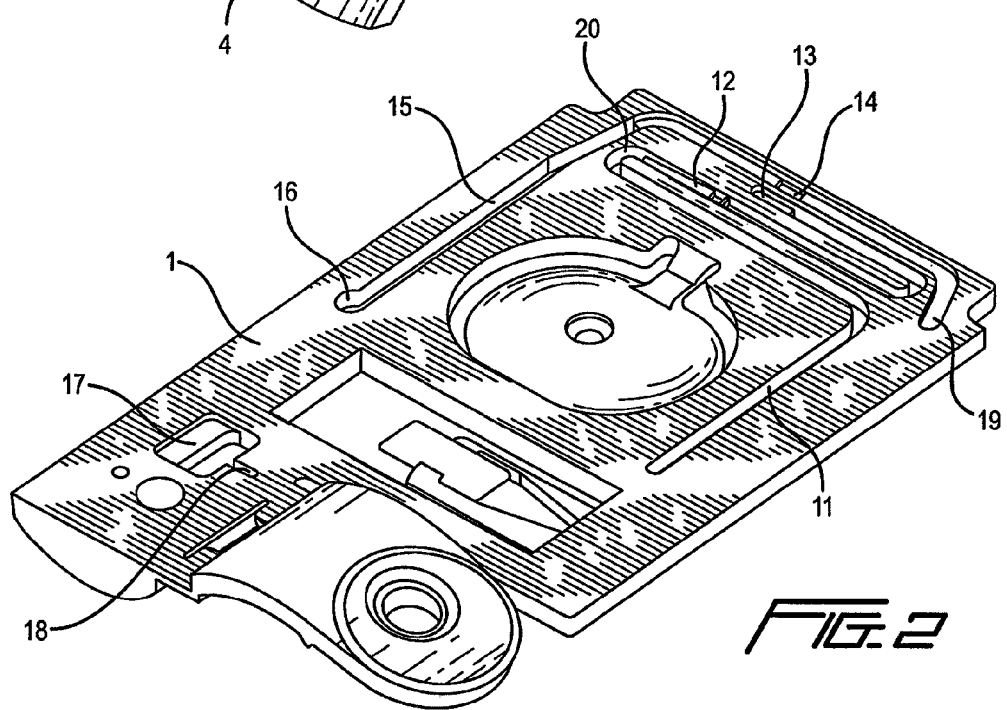
FIG. 2 is an isometric bottom view of an immunosensor cartridge cover.

Referring to the Figures, the cartridge of the present invention comprises a cover, FIGS. 1, 2, a base, FIG. 4, and a thin-film adhesive gasket, FIG. 3, disposed between the base and the cover. Referring now to FIG. 1, the cover 1 is made of a rigid material, preferably plastic, and capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. The cover further comprises two paddles 6, 7, that are moveable relative to the body of the cover, and which are attached to it by flexible hinge regions 5, 10. In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 cut therein. The cartridge is adapted for insertion into a reading apparatus, and therefore has a plurality of mechanical and electrical connections for this purpose. It should also be apparent that manual operation of the cartridge is possible. Thus, upon insertion of the cartridge into a reading apparatus, the gasket transmits pressure onto a fluid-containing foil pack filled with approximately 130 uL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge are used to inject one or more segments into the analysis fluid at controlled positions within the analysis conduit. These segments are used to help wash the sensor surface and the surrounding conduit with a minimum of fluid.

The cover further comprises a hole covered by a thin pliable film 8. In operation, pressure exerted upon the film expels one or more air segments into a conduit 20 through a small hole 28 in the gasket.

Referring to FIG. 2, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between conduits 11, 15. A recess 17 in the base provides a pathway for air in conduit 34 to pass to conduit 34 through hole 27 in the gasket.

Referring to FIG. 3, thin-film gasket 21 comprises various holes and slits to facilitate transfer of fluid between conduits within the base and the cover, and to allow the gasket to deform under pressure where necessary. Thus, hole 24 permits fluid to flow from conduit 11 into waste chamber 44; hole 25 comprises a capillary stop between conduits 34 and 11; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the plurality of electrodes that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor.

Referring to FIG. 4, conduit 34 is the sample holding chamber that connects the sample entry port 4 to first conduit 11 in the assembled cartridge. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

The location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed. This arrangement is therefore one possible embodiment of a metering means for delivering a metered amount of an unmetered sample into the conduits of the cartridge.

In the present cartridge, a means for metering a sample segment is provide in the base plastic part. The segment size is controlled by the size of the compartment in the base and the position of the capillary stop and air pipe holes in the tape gasket. This volume can be readily varied from 2 to 200 microliters. Expansion of this range of sample sizes is possible within the context of the present invention.

The fluid is pushed through a pre-analytical conduit 11 that can be used to amend a reagent (e.g., particles or soluble molecules) into the sample prior to its presentation at the sensor conduit 19. Alternatively, the amending reagent may be located in portion 15, beyond portion 16. Pushing the sample through the pre-analytical conduit also serves to introduce tension into the diaphragm pump paddle 7 which improves its responsiveness for actuation of fluid displacement.

In some assays, metering is advantageous if quantitation of the analyte is required. A waste chamber is provided, 44, for sample and/or fluid that is expelled from the conduit, to prevent contamination of the outside surfaces of the cartridge. A vent connecting the waste chamber to the external atmosphere is also provided, 45. A feature of the cartridge is that once a sample is loaded, analysis can be completed and the cartridge discarded without the operator or others contacting the sample.

Figure 5:
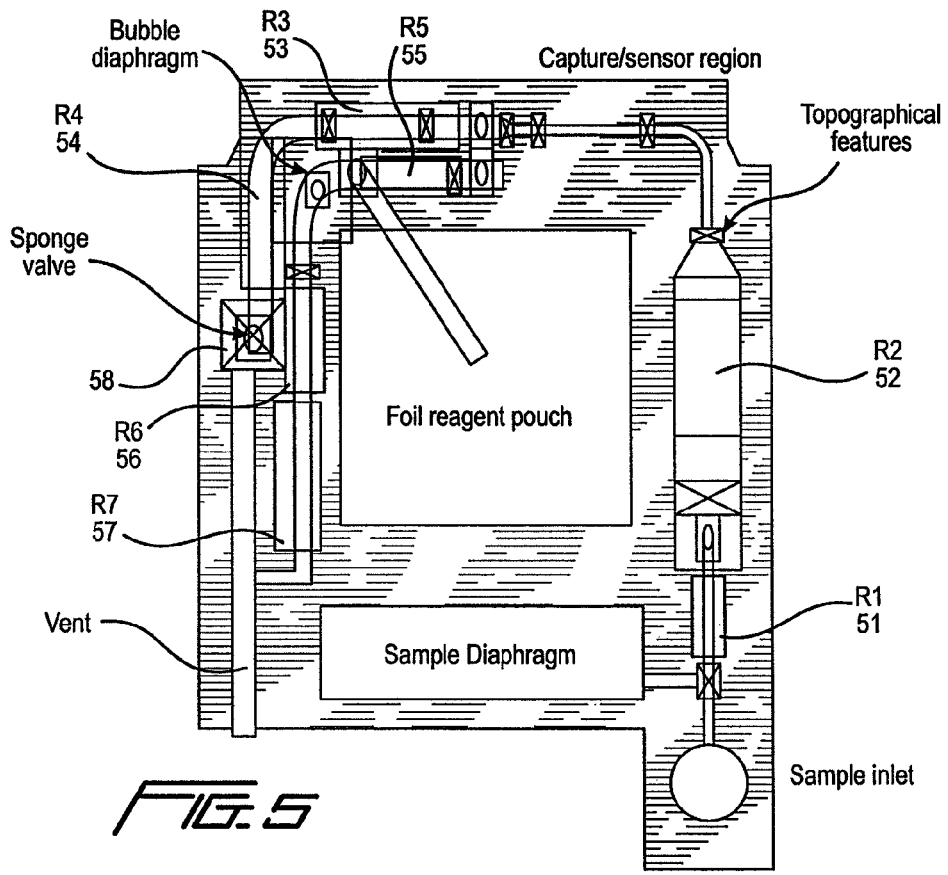
FIG. 5 is a schematic view of the layout of an immunosensor cartridge.

Referring now to FIG. 5, a schematic diagram of the features of a cartridge and components is provided, wherein 51-57 are portions of the conduits and sample chamber that can optionally be coated with dry reagents to amend a sample or fluid. The sample or fluid is passed at least once over the dry reagent to dissolve it. Reagents used to amend samples or fluid within the cartridge include antibody-enzyme conjugates, or blocking agents that prevent either specific or non-specific binding reactions among assay compounds. A surface coating that is not soluble but helps prevent non-specific adsorption of assay components to the inner surfaces of the cartridges can also be provided.

Within a segment of sample or fluid, an amending substance can be preferentially dissolved and concentrated within a predetermined region of the segment. This is achieved through control of the position and movement of the segment. Thus, for example, if only a portion of a segment, such as the leading edge, is reciprocated over the amended substance, then a high local concentration of the substance can be achieved close to the leading edge. Alternatively, if an homogenous distribution of the substance is desired, for example if a known concentration of an amending substance is required for a quantitative analysis, then further reciprocation of the sample or fluid will result in mixing and an even distribution.

In specific embodiments, a closeable valve is provided between the first conduit and the waste chamber. In one embodiment, this valve, 58, is comprised of a dried sponge material that is coated with an impermeable substance. In operation, contacting the sponge material with the sample or a fluid results in swelling of the sponge to fill the cavity 41, thereby substantially blocking further flow of liquid into the waste chamber 44. Furthermore, the wetted valve also blocks the flow of air between the first conduit and the waste chamber, which permits the first pump means connected to the sample chamber to displace fluid within the second conduit, and to displace fluid from the second conduit into the first conduit in the following manner. After the sample is exposed to the sensor for a controlled time, the sample is moved into the post-analytical conduit 19 where it can be amended with another reagent. It can then be moved back to the sensor and a second reaction period can begin. Alternately, the post-analysis conduit can serve simply to separate the sample segment from the sensor. Within this post-analysis conduit is a single closeable valve which connects the air vent of the sensor conduit to the diaphragm air pump. When this valve closes, the sample is locked in the post analytical conduit and cannot be moved back to the sensor chip. There are several different design examples for this valve that are encompassed within the present invention. Some designs are activated mechanically while others activate on liquid contact. Other types of closeable valve that are encompassed by the present invention include, but are not limited to; a flexible flap held in an open position by a soluble glue or a gelling polymer that dissolves or swells upon contact with a fluid or sample thus causing the flap to close; and alternatively, in one specific embodiment, a thin layer of a porous paper or similar material interposed between a conduit and either the waste chamber or ambient air such that the paper is permeable to air while dry but impermeable when wet. In the latter case it is not necessary that the closeable valve be interposed between a conduit and the waste chamber: the valve passes little to no liquid before closing and so the valve is appropriately placed when positioned between a conduit and the ambient air surrounding the cartridge. In practical construction, a piece of filter paper is placed on an opening in the tape gasket in the fluid path to be controlled. Air can readily move through this media to allow fluid to be moved through the fluid path. When the fluid is pushed over this filter, the filter media becomes filled with liquid and further motion through the fluid path is stopped. Once the filter become wet, significant pressures would be required to move liquid through the pores of the filter. Air flow through the filter is also prevented because of the higher pressure required to push the liquid out of the filter, typically termed bubble pressure. This valve embodiment requires very little liquid to actuate the valve, and actuation occurs rapidly and reliably. Materials, their dimensions, porosity, wettability, swelling characteristics and related parameters are selected to provide for rapid closure, within one second or more slowly, e.g., up to 60 seconds, after first contacting the sample, depending on the specific desired closure time.

Alternatively, the closeable valve is a mechanical valve. In this embodiment, a latex diaphragm is placed in the bottom of the air bladder on top of a specially constructed well. The well contains two openings which fluidically connect the air vent to the sample conduit. As the analyzer plunger pushes to the bottom of the air bladder, it presses on this latex diaphragm which is adhesive backed and seals the connection between the two holes. This blocks the sample's air vent, locking the sample in place.

Figure 6:
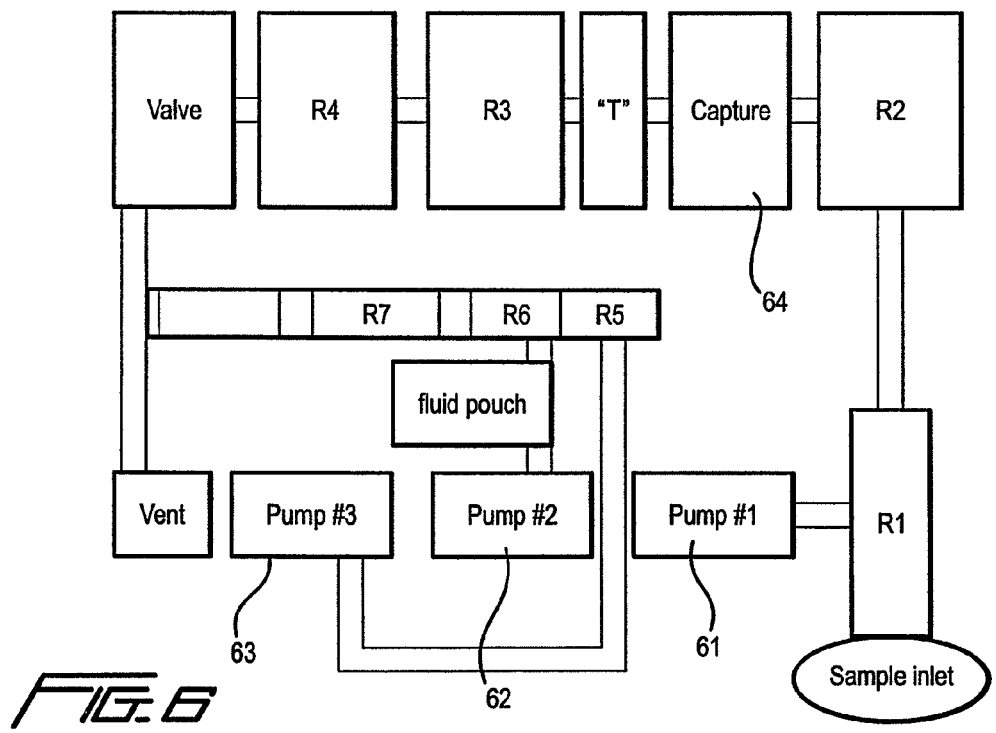
FIG. 6 is a schematic view of the fluid and air paths within an immunosensor cartridge, including sites for amending fluids with dry reagents.

Referring now to FIG. 6, which illustrates the schematic layout of an immunosensor cartridge, there are provided three pump means, 61-63. While these pumps have been described in terms of specific embodiments, it will be readily understood that any pump means capable of performing the respective functions of pump means 61-63 may be used within the present invention. Thus, pump means 1, 61, must be capable of displacing the sample from the sample holding chamber into the first conduit; pump means 2, 62, must be capable of displacing fluid within the second conduit; and pump means 3, 63, must be capable of inserting at least one segment into the second conduit. Other types of pump which are envisaged in the present application include, but are not limited to, an air sac contacting a pneumatic means whereby pressure is applied to said air sac, a flexible diaphragm, a piston and cylinder, an electrodynamic pump, and a sonic pump. With reference to pump means 3, 63, the term "pump means" includes all methods by which one or more segments are inserted into the second conduit, such as a pneumatic means for displacing air from an air sac, a dry chemical that produces a gas when dissolved, or a plurality of electrolysis electrodes operably connected to a current source. In a specific embodiment, the segment is produced using a mechanical segment generating diaphragm that may have more than one air bladder or chamber. The well 8 has a single opening which connects the inner diaphragm pump and the fluid filled conduit into which a segment is to be injected 20. The diaphragm can be segmented to produce multiple segments, each injected in a specific location within a fluid filled conduit.

In alternative embodiments, a segment is injected using a passive feature. A well in the base of the cartridge is sealed by tape gasket. The tape gasket covering the well has two small holes on either end. One hole is open while the other is covered with a filter material which wets upon contact with a fluid. The well is filled with a loose hydrophilic material such as a cellulose fiber filter, paper filter or glass fiber filter. This hydrophilic material draws the liquid into the well in the base via capillary action, displacing the air which was formerly in the well. The air is expelled through the opening in the tape gasket creating a segment whose volume is determined by the volume of the well and the void volume of the loose hydrophilic material. The filter used to cover one of the inlets to the well in the base can be chosen to meter the rate at which the fluid fills the well and thereby control the rate at which the segment is injected into the conduit in the cover. This passive feature permits any number of controlled segments to be injected at specific locations within a fluid path and requires a minimum of space.

The present invention will be better understood with reference to the specific embodiments set forth in the following examples.

Example 1

Figure 7:
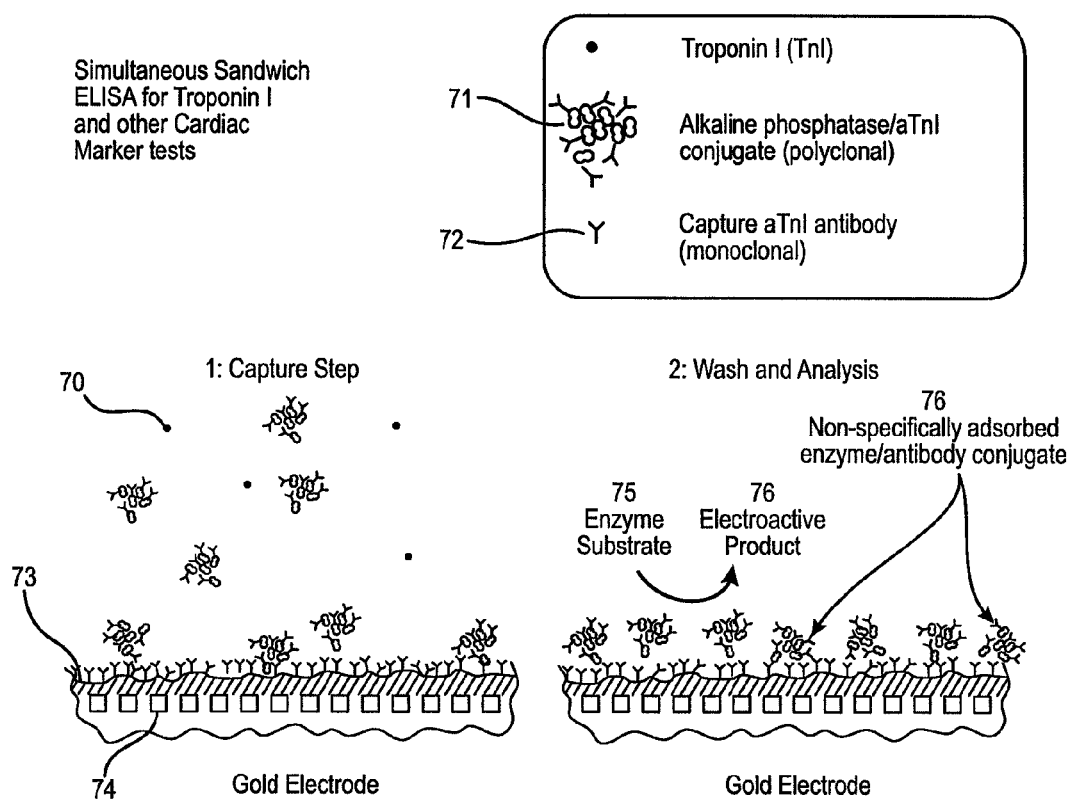
FIG. 7 illustrates the principle of operation of an electrochemical immunosensor.

Referring now to FIG. 7, which illustrates the principle of an amperometric immunoassay according to specific embodiments of the present invention for determination of troponin I (TnI), a marker of cardiac function. A blood sample, for example, is introduced into the sample holding chamber of a cartridge of the present invention, and is amended by a conjugate molecule comprising alkaline phosphatase enzyme (AP) covalently attached to a polyclonal anti-troponin I antibody (aTnI) 71. This conjugate specifically binds to the TnI, 70, in the blood sample, producing a complex made up of TnI bound to the AP-aTnI conjugate. In a capture step, this complex binds to the capture aTnI antibody 72 attached on, or close to, the immunosensor. The sensor chip has a conductivity sensor which is used to monitor when the sample reaches the sensor chip. The time of arrival of the fluid can be used to detect leaks within the cartridge: a delay in arrival signals a leak. The position of the sample segment within the sensor conduit can be actively controlled using the edge of the fluid as a marker. As the sample/air interface crosses the conductivity sensor, a precise signal is generated which can be used as a fluid marker from which controlled fluid excursions can be executed. The fluid segment is preferentially oscillated edge-to-edge over the sensor in order to present the entire sample to the sensor surface. A second reagent can be introduced in the sensor conduit beyond the sensor chip, which becomes homogenously distributed during the fluid oscillations.

The sensor chip contains a capture region or regions coated with antibodies for the analyte of interest. These capture regions are defined by a hydrophobic ring of polyimide or another photolithographically produced layer. A microdroplet or several microdroplets (approximately 5-40 nanoliters in size) containing antibodies in some form, for example bound to latex microspheres, is dispensed on the surface of the sensor. The photodefined ring contains this aqueous droplet allowing the antibody coated region to be localized to a precision of a few microns. The capture region can be made from 0.03 to roughly 2 square millimeters in size. The upper end of this size is limited by the size of the conduit and sensor in present embodiments, and is not a limitation of the invention.

Thus, the gold electrode 74 is coated with a biolayer 73 comprising a covalently attached anti-troponin I antibody, to which the TnI/AP-aTnI complex binds. AP is thereby immobilized close to the electrode in proportion to the amount of TnI initially present in the sample. In addition to specific binding, the enzyme-antibody conjugate may bind non-specifically to the sensor. Non-specific binding provides a background signal from the sensor that is undesirable and preferably is minimized. As described above, the rinsing protocols, and in particular the use of segmented fluid to rinse the sensor, provide efficient means to minimize this background signal. In a second step subsequent to the rinsing step, a substrate 75 that is hydrolyzed by, for example, alkaline phosphatase to produce an electroactive product 76 is presented to the sensor. In specific embodiments the substrate is comprised of a phosphorylated ferrocene or p-aminophenol. The amperometric electrode is either clamped at a fixed electrochemical potential sufficient to oxidize or reduce a product of the hydrolyzed substrate but not the substrate directly, or the potential is swept one or more times through an appropriate range. Optionally, a second electrode may be coated with a layer where the complex of TnI/AP-aTnI is made during manufacture, to act as a reference sensor or calibration means for the measurement.

In the present example, the sensor comprises two amperometric electrodes which are used to detect the enzymatically produced 4-aminophenol from the reaction of 4-aminophenylphosphate with the enzyme label alkaline phosphatase. The electrodes are preferably produced from gold surfaces coated with a photodefined layer of polyimide. Regularly spaced opening in the insulating polyimide layer define a grid of small gold electrodes at which the 4-aminophenol is oxidized in a 2 electron per molecule reaction. Sensor electrodes further comprise a biolayer, while reference electrodes can be constructed, for example, from gold electrodes lacking a biolayer, or from silver electrodes, or other suitable material. Different biolayers can provide each electrode with the ability to sense a different analyte.

Substrates, such as p-aminophenol species, can be chosen such that the $E_{1/2}$ of the substrate and product differ substantially. Preferably, the voltammetric half-wave potential ($E_{1/2}$) of the substrate is substantially higher (more positive) than that of the product. When the condition is met, the product can be selectively electrochemically measured in the presence of the substrate.

The size and spacing of the electrode play an important role in determining the sensitivity and background signal. The important parameters in the grid are the percentage of exposed metal and the spacing between the active electrodes. The position of the electrode can be directly underneath the antibody capture region or offset from the capture region by a controlled distance. The actual amperometric signal of the electrodes depends on the positioning of the sensors relative to the antibody capture site and the motion of the fluid during the analysis. A current at the electrode is recorded that depends upon the amount of electroactive product in the vicinity of the sensor.

The detection of alkaline phosphatase activity in this example relies on a measurement of the 4-aminophenol oxidation current. This is achieved at a potential of about +60 mV versus the Ag/AgCl ground chip. The exact form of detection used depends on the sensor configuration. In one version of the sensor, the array of gold microelectrodes is located directly beneath the antibody capture region. When the analysis fluid is pulled over this sensor, enzyme located on the capture site converts the 4-aminophenylphosphate to 4-aminophenol in an enzyme limited reaction. The concentration of the 4-aminophenylphosphate is selected to be in excess, e.g., 10 times the Km value. The analysis solution is 0.1 M in diethanolamine, 1.0 M NaCl, buffered to a pH of 9.8. Additionally, the analysis solution contains 0.5 mM MgCl which is a cofactor for the enzyme. Alternatively, a carbonate buffer has the desired properties.

In another electrode geometry embodiment, the electrode is located a few hundred microns away from the capture region. When a fresh segment of analysis fluid is pulled over the capture region, the enzyme product builds with no loss due to electrode reactions. After a time, the solution is slowly pulled from the capture region over the detector electrode resulting in a current spike from which the enzyme activity can be determined.

An important consideration in the sensitive detection of alkaline phosphatase activity is the non-4-aminophenol current associated with background oxidations and reductions occurring at the gold sensor. Gold sensors tend to give significant oxidation currents in basic buffers at these potentials. The background current is largely dependent on the buffer concentration, the area of the gold electrode (exposed area), surface pretreatments and the nature of the buffer used. Diethanolamine is a particularly good activating buffer for alkaline phosphatase. At molar concentrations, the enzymatic rate is increased by about three times over a non-activating buffer such as carbonate.

In alternative embodiments, the enzyme conjugated to an antibody or other analyte-binding molecule is urease, and the substrate is urea. Ammonium ions produced by the hydrolysis of urea are detected in this embodiment by the use of an ammonium sensitive electrode. Ammonium-specific electrodes are well-known to those of skill in the art. A suitable microfabricated ammonium ion-selective electrode is disclosed in U.S. Pat. No. 5,200,051, incorporated herein by reference. Other enzymes that react with a substrate to produce an ion are known in the art, as are other ion sensors for use therewith. For example, phosphate produced from an alkaline phosphatase substrate can be detected at a phosphate ion-selective electrode.

Figure 8:
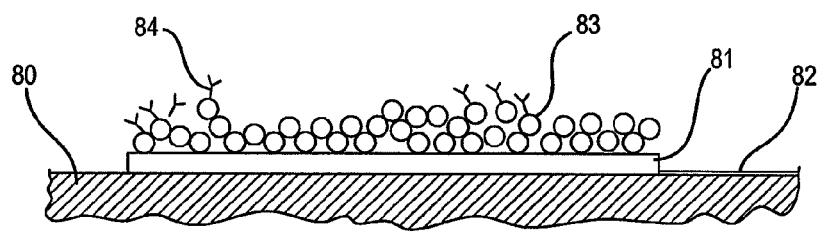
FIG. 8 is a side view of the construction of an electrochemical immunosensor with antibody-labeled particles not drawn to scale.
Figure 8:
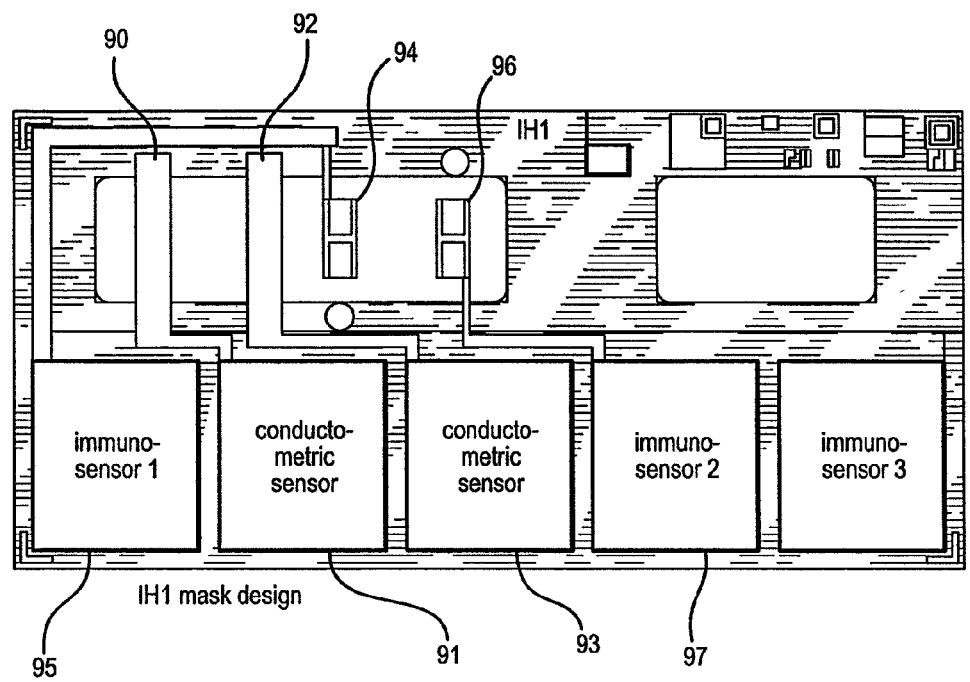

Referring now to FIG. 8, there is illustrated the construction of an embodiment of a microfabricated immunosensor. Preferably a planar non-conducting substrate is provided, 80, onto which is deposited a conducting layer 81 by conventional means or microfabrication known to those of skill in the art. The conducting material is preferably a noble metal such as gold or platinum, although other unreactive metals such as iridium may also be used, as may non-metallic electrodes of graphite, conductive polymer, or other materials. An electrical connection 82 is also provided. A biolayer 83 is deposited onto at least a portion of the electrode. In the present disclosure, a biolayer means a porous layer comprising on its surface a sufficient amount of a molecule 84 that can either bind to an analyte of interest, or respond to the presence of such analyte by producing a change that is capable of measurement. Optionally, a permselective screening layer may be interposed between the electrode and the biolayer to screen electrochemical interferents as described in U.S. Pat. No. 5,200,051.

In specific embodiments, a biolayer is constructed from latex beads of specific diameter in the range of about 0.001 to 50 microns. The beads are modified by covalent attachment of any suitable molecule consistent with the above definition of a biolayer. Many methods of attachment exist in the art, including providing amine reactive N-hydroxysuccinimide ester groups for the facile coupling of lysine or N-terminal amine groups of proteins. In specific embodiments, the biomolecule is chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In most specific embodiments, the biomolecule is an antibody selected to bind one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. Preferably, the biomolecule binds to the analyte specifically and has an affinity constant for binding analyte ligand of about $10^7$ to $10^{15}$ $M^{-1}$.

In one embodiment, the biolayer, comprising beads having surfaces that are covalently modified by a suitable molecule, is affixed to the sensor by the following method. A microdispensing needle is used to deposit onto the sensor surface a small droplet, preferably about 20 nL, of a suspension of modified beads. The droplet is permitted to dry, which results in a coating of the beads on the surface that resists displacement during use.

In addition to immunosensors in which the biolayer is in a fixed position relative to an amperometric sensor, the present invention also envisages embodiments in which the biolayer is coated upon particles that are mobile. The cartridge can contain mobile microparticles capable of interacting with an analyte, for example magnetic particles that are localized to an amperometric electrode subsequent to a capture step, whereby magnetic forces are used to concentrate the particles at the electrode for measurement. One advantage of mobile microparticles in the present invention is that their motion in the sample or fluid accelerates binding reactions, making the capture step of the assay faster. For embodiments using non-magnetic mobile microparticles, a porous filter is used to trap the beads at the electrode.

Referring now to FIG. 9, there is illustrated a mask design for several electrodes upon a single substrate. By masking and etching techniques, independent electrodes and leads can be deposited. Thus, a plurality of immunosensors, 94 and 96, and conductimetric sensors, 90 and 92, are provided in a compact area at low cost, together with their respective connecting pads, 91, 93, 95, and 97, for effecting electrical connection to the reading apparatus. In principle, a very large array of sensors can be assembled in this way, each sensitive to a different analyte or acting as a control sensor or reference immunosensor.

Specifically, immunosensors are prepared as follows. Silicon wafers are thermally oxidized to form approximately a 1 micron insulating oxide layer. A titanium/tungsten layer is sputtered onto the oxide layer to a preferable thickness of between 100-1000 Angstroms, followed by a layer of gold that is most preferably 800 Angstroms thick. Next, a photoresist is spun onto the wafer and is dried and baked appropriately. The surface is then exposed using a contact mask, such as a mask corresponding to that illustrated in FIG. 9. The latent image is developed, and the wafer is exposed to a gold-etchant. The patterned gold layer is coated with a photodefinable polyimide, suitably baked, exposed using a contact mask, developed, cleaned in an $O_2$ plasma, and preferably imidized at 350° C. for 5 hours. An optional metallization of the back side of the wafer may be performed to act as a resistive heating element, where the immunosensor is to be used in a thermostatted format. The surface is then printed with antibody-coated particles. Droplets, preferably of about 20 nL volume and containing 1% solid content in deionized water, are deposited onto the sensor region and are dried in place by air drying. Optionally, an antibody stabilization reagent (supplied by SurModica Corp. or AET Ltd.) is overcoated onto the sensor.

Drying the particles causes them to adhere to the surface in a manner that prevents dissolution in either sample or fluid containing a substrate. This method provides a reliable and reproducible immobilization process suitable for manufacturing sensor chips in high volume.

Figure 10:
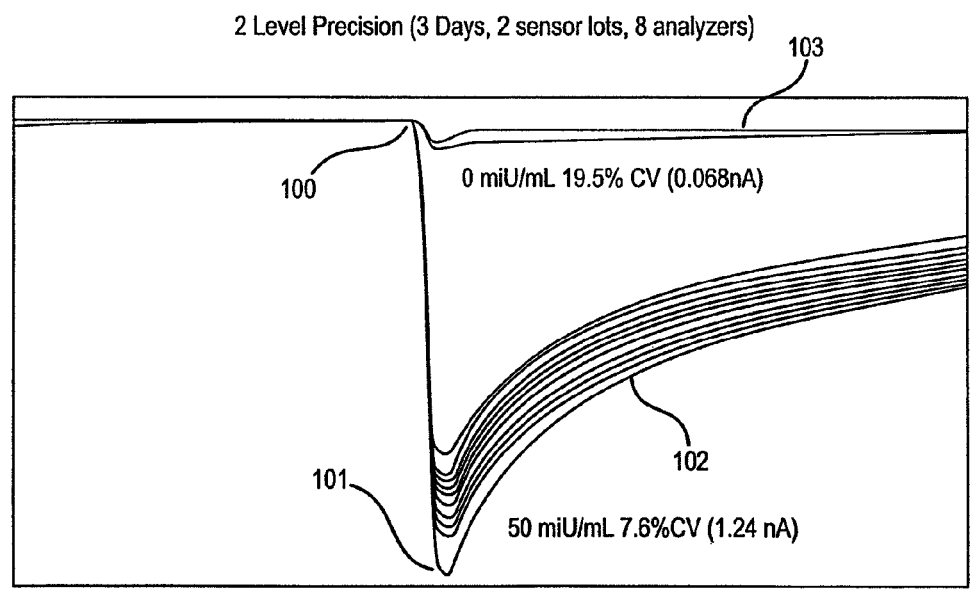
FIG. 10 illustrates the electrochemical responses of immunosensors constructed with an anti-HCG antibody when presented with 50 mIU/mL of HCG.
Figure 13:
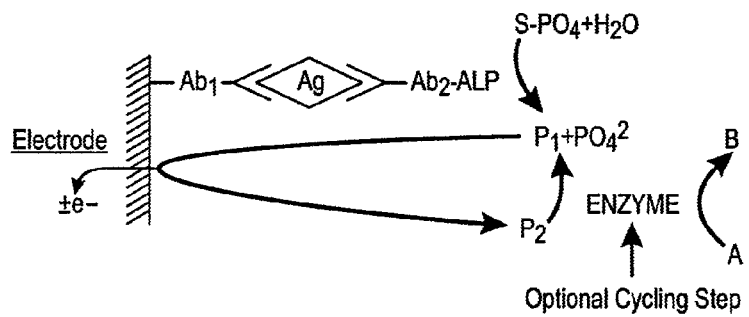
FIG. 13 is a schematic illustration of enzymatic regeneration of an electroactive species.

Referring now to FIG. 10, there are illustrated results obtained for analysis of samples containing 0 or 50 miU/mL human chorionic gonadotrophin (HCG) and an HCG-sensitive amperometric immunosensor. At time 100, a solution containing a p-aminophenol phosphate is supplied to a sensor which is previously treated with HCG and an anti-HCG polyclonal antibody conjugated to alkaline phosphatase. As the substrate is hydrolyzed by alkaline phosphatase, a current increases to a maximum 101, and thereafter declines 102, as substrate within the diffusion volume of the sensor is depleted and oxidized p-aminophenol accumulates. Good reproducibility is obtained between sensors, as shown by the output signal characteristics of individual single-use sensors. In operation, displacement of the fluid containing the enzyme substrate provides fresh substrate to the electrode surface, and also removes products, so that multiple readings are easily obtained for a single sample. In an alternative embodiment, the signal at the electrode is augmented by enzymatic regeneration of the electroactive species in the vicinity of the electrode. In a specific embodiment, a phosphorylated ferrocene is used as the substrate for alkaline phosphatase attached to the antibody. Hydrolysis yields a ferrocene product, which is oxidized and detected at the electrode. In a second step, glucose oxidase enzyme and glucose are used to re-reduce the electrochemically oxidized ferrocene, with a consequent increase in the current and detection sensitivity. Referring now to FIG. 13, an electrode 130 oxidizes or reduces the electroactive product 132 of alkaline phosphatase immobilized as a complex 131 on or close to the electrode surface. In a second step, the electroactive species 132 is regenerated from the product 133 by the catalytic action of enzyme 134. This cycling reaction increases the concentration of electroactive species 132 in proximity to the electrode surface 130, and thereby increases the current recorded at the electrode.

Figure 11:
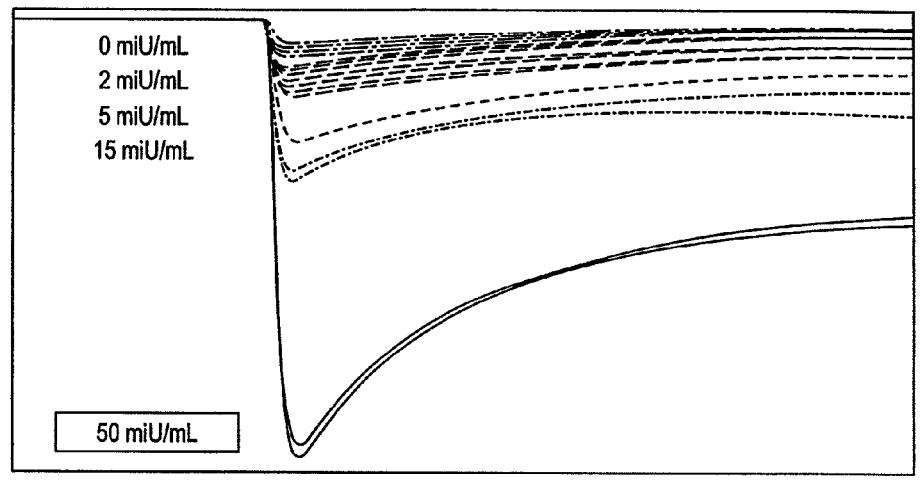
FIG. 11 illustrates the electrochemical response (current versus time) of an immunosensor constructed with an anti-HCG antibody when presented with various amounts of HCG from 0 to 50 mIU/mL.
Figure 12:
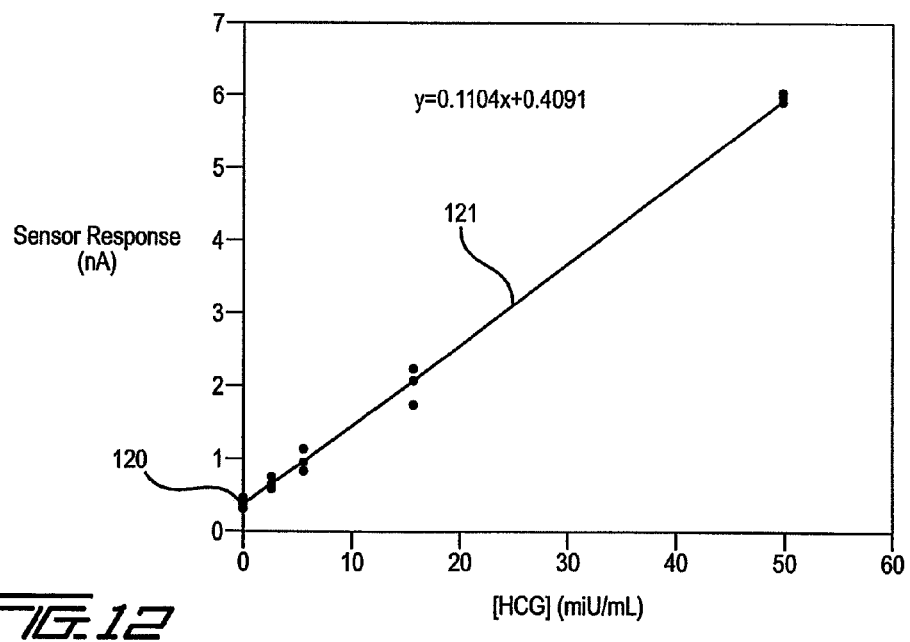
FIG. 12 illustrates the maximum current obtained when an immunosensor constructed with an anti-HCG antibody is presented with various amounts of HCG.

Referring now to FIG. 11, there is shown dose-response results obtained using HCG and an HCG-responsive amperometric immunosensor. Amounts of HCG equivalent to 0 to 50 miU/mL are allowed to bind to the immobilized antibody attached to the electrode, as in FIG. 10. Referring now to FIG. 12, good linearity, and 121, of the response of the peak sensor current with increasing HCG is found. Thus, it is demonstrated that this embodiment can precisely and rapidly quantify HCG in a sample.

Example 2

Method of Use of a Cartridge

An unmetered fluid sample is introduced into sample chamber 34 of a cartridge according to claim 1, through sample entry port 4. Capillary stop 25 prevents passage of the sample into conduit 11 at this stage, and conduit 34 is filled with the sample. Lid 2 or element 200 is closed to prevent leakage of the sample from the cartridge. The cartridge is then inserted into a reading apparatus, such as that disclosed in U.S. Pat. No. 5,821,399 to Zelin, which is hereby incorporated by reference. Insertion of the cartridge into a reading apparatus activates the mechanism which punctures a fluid-containing package located at 42 when the package is pressed against spike 38. Fluid is thereby expelled into the second conduit, arriving in sequence at 39, 20, 12 and 11. The constriction at 12 prevents further movement of fluid because residual hydrostatic pressure is dissipated by the flow of fluid via second conduit portion 11 into the waste chamber 44. In a second step, operation of a pump means applies pressure to air-bladder 43, forcing air through conduit 40, through cutaways 17 and 18, and into conduit 34 at a predetermined location 27. Capillary stop 25 and location 27 delimit a metered portion of the original sample. While the sample is within sample chamber 34, it is optionally amended with a compound or compounds present initially as a dry coating on the inner surface of the chamber. The metered portion of the sample is then expelled through the capillary stop by air pressure produced within air bladder 43. The sample passes into conduit 15 and into contact with the analyte sensor or sensors located within cutaway 35.

In embodiments employing an immunosensor located within cutout 35, the sample is amended prior to arriving at the sensor by, for example, an enzyme-antibody conjugate. An antibody that binds the analyte of interest is covalently attached to an enzyme that can generate a redox active substance close to an amperometric electrode. In specific embodiments, the enzyme may be alkaline phosphatase, which hydrolyzes certain organophosphate compounds, such as derivatives of p-aminophenol that liberate redox-active compounds when hydrolyzed. However, any enzyme capable of producing, destroying, or altering any compound that may be detected by a sensor may be employed in conjunction with a matching sensor. For example, antibody-urease conjugate may be used together with an ammonium sensor. Thus, the enzyme-antibody conjugate or conjugates amends the sample and binds to the analyte of interest. The immunosensor can comprise immobilized antibody that binds to an analyte of interest. When the amended sample passes over the immunosensor, the analyte of interest binds to the sensor, together with antibody-enzyme conjugate to which it is attached.

To promote efficient binding of the analyte to the sensor, the sample containing the analyte is optionally passed repeatedly over the sensor in an oscillatory motion. Preferably, an oscillation frequency of between about 0.2 and 2 Hz is used, most preferably 0.7 Hz. Thus enzyme is brought into close proximity to the amperometric electrode surface in proportion to the amount of analyte present in the sample.

Once an opportunity for the analyte/enzyme-antibody conjugate complex to bind to the immunosensor has been provided, the sample is ejected by further pressure applied to air bladder 43, and the sample passes to waste chamber 44.

A wash step next removes non-specifically bound enzyme-conjugate from the sensor chamber. Fluid in the second conduct is moved by a pump means 43, into contact with the sensors. The analysis fluid is pulled slowly until the first air segment is detected at a conductivity sensor.

Figure 14:
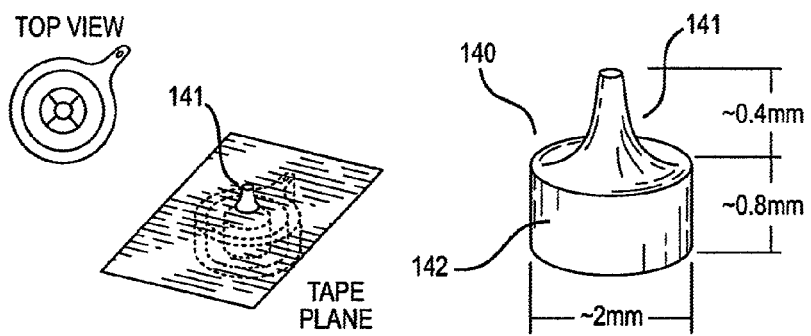
FIG. 14 illustrates segment forming means.

The air segment or segment can be produced within a conduit by any suitable means, including but not limited to, passive means, as shown in FIG. 14 and described below; active means including a transient lowering of the pressure within a conduit using pump means whereby air is drawn into the conduit through a flap or valve; or by dissolving a compound pre-positioned within a conduit that liberates a gas upon contacting fluid in the conduit, where such compound may include a carbonate, bicarbonate or the like. This segment is extremely effective at clearing the sample-contaminated fluid from conduit 15. The efficiency of the rinsing of the sensor region is greatly enhanced by the introduction of one or more air segments into the second conduit as described. The leading and/or trailing edges of air segments are passed one or more times over the sensors to rinse and resuspend extraneous material that may have been deposited from the sample. Extraneous material includes any material other than specifically bound analyte or analyte/antibody-enzyme conjugate complex. However, it is an object of the invention that the rinsing is not sufficiently protracted or vigorous as to promote dissociation of specifically bound analyte or analyte/antibody-enzyme conjugate complex from the sensor.

A second advantage of introducing air segments into the fluid is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate. After the front edge washing, the analysis fluid is pulled slowly until the first air segment is detected at a conductivity sensor. This segment is extremely effective at clearing the sample-contaminated fluid which was mixed in with the first analysis fluid sample.

A second advantage of introducing air segments into conduit two is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate.

For measurement, a new portion of fluid is placed over the sensors, and the current or potential, as appropriate to the mode of operation, is recorded as a function of time.

Example 3

Method of Use of a Cartridge

Use of a cartridge with a closeable valve, preferably located between the sensor chamber and the waste chamber, is herein illustrated by a specific embodiment in which the concentration of HCG is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the sensors through pads 91, 93, 95, and 97, and performs certain diagnostic tests. Insertion of the cartridge perforates the foil pouch introducing fluid into the second conduit as previously described. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the analyte determination.

Between t=1.5 and t=6.75, a metered portion of the sample, preferably between 4 and 200 µl, more preferably between 4 and 20 µl, and most preferably 7 µl, is used to contact the sensor as described in EXAMPLE 2. The edges defining the forward and trailing edges of the sample are reciprocally moved over the sensor region at a frequency that is preferably between 0.2 to 2.0 Hz, and is most preferably 0.7 Hz. During this time, the enzyme-antibody conjugate dissolves within the sample, as previously described. The amount of enzyme-antibody conjugate that is coated onto the conduit is selected to yield a concentration when dissolved that is preferably higher than the highest anticipated HCG concentration, and is most preferably six times higher than the highest anticipated HCG concentration in the sample.

Between t=6.75 and t=10.0 the sample is moved into the waste chamber via closeable valve 41, wetting the closeable valve and causing it to close as previously described. The seal created by the closing of the valve permits the first pump means to be used to control motion of fluid from conduit 11 to conduit 15. After the valve closes and the any remaining sample is locked in the post analysis conduit, the analyzer plunger retracts from the flexible diaphragm of the pump mean creating a partial vacuum in the sensor conduit. This forces the analysis fluid through the small hole in the tape gasket 31 and into a short transecting conduit in the base, 13, 14. The analysis fluid is pulled further and the front edge of the analysis fluid is oscillated across the surface of the sensor chip in order to shear the sample near the walls of the conduit. A conductivity sensor on the sensor chip is used to control this process. The efficiency of the process is monitored using the amperometric sensors through the removal of unbound enzyme-antibody conjugate which enhances the oxidation current measured at the electrode when the enzyme substrate, 4-aminophenyl phosphate is also present. The amperometric electrodes are polarized to 0.06 V versus the silver chloride reference-ground electrode. In this embodiment, the fluid is composed of a 0.1 M carbonate or diethanolamine buffer, at pH 9.8, with 1 mM $MgCl_2$, 1.0 M NaCl, 10 mM 4-aminophenylphosphate, and 10 µM NaI. The efficiency of the wash is optimally further enhanced by introduction into the fluid of one or more segments that segment the fluid within the conduit as previously described. The air segment may be introduced by either active or passive means. Referring now to FIG. 14, there is illustrated the construction of a specific means for passively introducing an air segment into said fluid. Within the base of the immunosensor is recess 140 comprising a tapered portion 141 and a cylindrical portion that are connected. The tapered portion is in fluid connection with a hole 142 of similar diameter in the tape gasket (FIG. 3) that separates the base (FIG. 4) and cover (FIGS. 1 and 2) of the assembled immunosensor cartridge. The recess contains an absorbent material that, upon contact with fluid, withdraws a small quantity of fluid from a conduit thereby passively introducing an air segment into the conduit. The volume of the recess and the amount and type of material within it may be adjusted to control the size of the air segment introduced. Specific materials include, but are not limited to, glass filter, a laminate comprising a 3 micron Versapor filter bonded by sucrose to a 60% viscose chiffon layer.

Fluid is forcibly moved towards sensor chip by the partial vacuum generated by reducing the mechanical pressure exerted upon paddle 6, causing the "T" region of the sensor channel in the vicinity of the transecting conduit to fill with analysis fluid. The T region of the sensor channel optionally has a higher channel height resulting a meniscus with a smaller radius of curvature. Further away from the T region towards the post-analytical conduit, the conduit height is optionally smaller. The analysis fluid passively flows from the T region towards this low conduit height region washing the conduit walls. This passive leak allows further effective washing of the T region using a minimal volume of fluid.

In this simple embodiment, the fluid located within the second conduit contains a substrate for the enzyme. In other embodiments, amendment of the fluid using dried substrate within the second conduit may be used.

Following the positioning of a final segment of fluid over the sensor, measurement of the sensor response is recorded and the concentration of analyte determined as described for Example 2. Specifically, at least one sensor reading of a sample is made by rapidly placing over the sensor a fresh portion of fluid containing a substrate for the enzyme. Rapid displacement both rinses away product previously formed, and provides now substrate to the electrode. Repetitive signals are averaged to produce a measurement of higher precision, and also to obtain a better statistical average of the baseline, represented by the current immediately following replacement of the solution over the sensor.

Example 4

Figure 15:
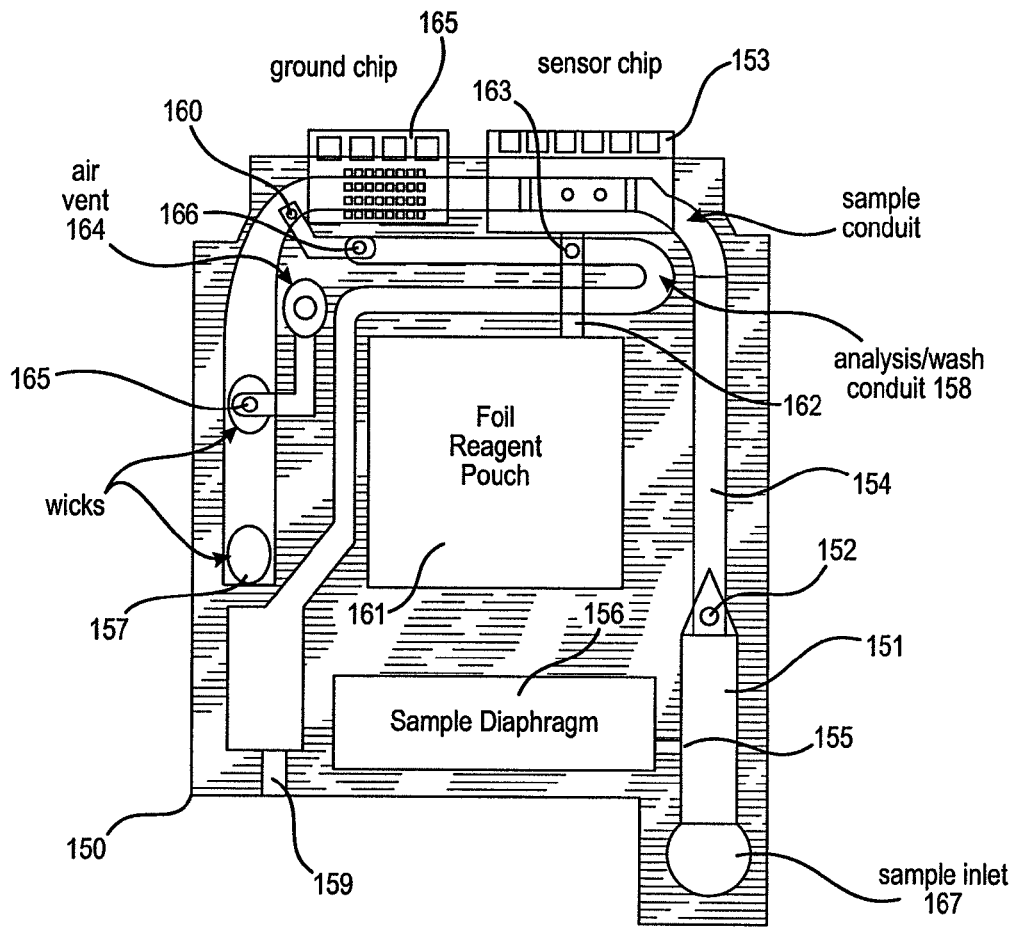
FIG. 15 is a top view of the preferred embodiment of an immunosensor cartridge.

Referring now to FIG. 15, there is shown a top view of an immunosensor cartridge. Cartridge 150 comprises a base and a top portion, preferably constructed of a plastic. The two portions are connected by a thin, adhesive gasket or thin pliable film. As in previous embodiments, the assembled cartridge comprises a sample chamber 151 into which a sample containing an analyte of interest is introduced via a sample inlet 152. A metered portion of the sample is delivered to the sensor chip 153, via the sample conduit 154 (first conduit) as before by the combined action of a capillary stop 152, preferably formed by a 0.012" laser cut hole in the gasket or film that connects the two portions of the cartridge, and an entry point 155 located at a predetermined point within the sample chamber whereby air introduced by the action of a pump means, such as a paddle pushing upon a sample diaphragm 156. After contacting the sensor to permit binding to occur, the sample is moved to vent 157, which contains a wicking material that absorbs the sample and thereby seals the vent closed to the further passage of liquid or air. The wicking material is preferably a cotton fiber material, a cellulose material, or other hydrophilic material having pores. It is important in the present application that the material is sufficiently absorbent (i.e., possesses sufficient wicking speed) that the valve closes within a time period that is commensurate with the subsequent withdrawal of the sample diaphragm actuating means described below, so that sample is not subsequently drawn back into the region of the sensor chip.

As in the specific embodiments, there is provided a wash conduit (second conduit) 158, connected at one end to a vent 159 and at the other end to the sample conduit at a point 160 of the sample conduit that is located between vent 157 and sensor chip 153. Upon insertion of the cartridge into a reading apparatus, a fluid is introduced into conduit 158. Preferably, the fluid is present initially within a foil pouch 161 that is punctured by a pin when an actuating means applies pressure upon the pouch. There is also provided a short conduit 162 that connects the fluid to conduit 154 via a small opening in the gasket 163. A second capillary stop initially prevents the fluid from reaching capillary stop 160, so that the fluid is retained within conduit 158.

After vent 157 has closed, the pump means is actuated, creating a lowered pressure within conduit 154. Air vent 164, preferably comprising a small flap cut in the gasket or a membrane that vibrates to provide an intermittent air stream, provides a means for air to enter conduit 158 via a second vent 165. The second vent 165 preferably also contains wicking material capable of closing the vent if wetted, which permits subsequent depression of sample diaphragm 156 to close vent 165, if required. Simultaneously with the actuation of sample diaphragm 156, fluid is drawn from conduit 158, through capillary stop 160, into conduit 154. Because the flow of fluid is interrupted by air entering vent 164, at least one air segment (a segment or stream of segments) is introduced.

Further withdrawal of sample diaphragm 156 draws the liquid containing at least one air segment back across the sensing surface of sensor chip 153. The presence of air-liquid boundaries within the liquid enhances the rinsing of the sensor chip surface to remove remaining sample. Preferably, the movement of the sample diaphragm 156 is controlled in conjunction with signals received from the conductivity electrodes housed within the sensor chip adjacent to the analyte sensors. In this way, the presence of liquid over the sensor is detected, and multiple readings can be performed by movement of the fluid in discrete steps.

It is advantageous in this embodiment to perform analyte measurements when only a thin film of fluid coats the sensors, ground chip 165, and a contiguous portion of the wall of conduit 154 between the sensors and ground electrode. A suitable film is obtained by withdrawing fluid by operation of the sample diaphragm 156, until the conductimetric sensor located next to the sensor indicates that bulk fluid is no longer present in that region of conduit 154. It has been found that measurement can be performed at very low (nA) currents, the potential drop that results from increased resistance of a thin film between ground chip and sensor chip (compared to bulk fluid), is not significant.

The ground chip 165 is preferably silver/silver chloride. It is advantageous, to avoid air segments, which easily form upon the relatively hydrophobic silver chloride surface, to pattern the ground chip as small regions of silver/silver chloride interspersed with more hydrophilic regions, such as a surface of silicon dioxide. Thus, a preferred ground electrode configuration comprises an array of silver/silver chloride squares densely arranged and interspersed with silicon dioxide. There is a further advantage in the avoidance of unintentional segments if the regions of silver/silver chloride are somewhat recessed.

Figure 16:
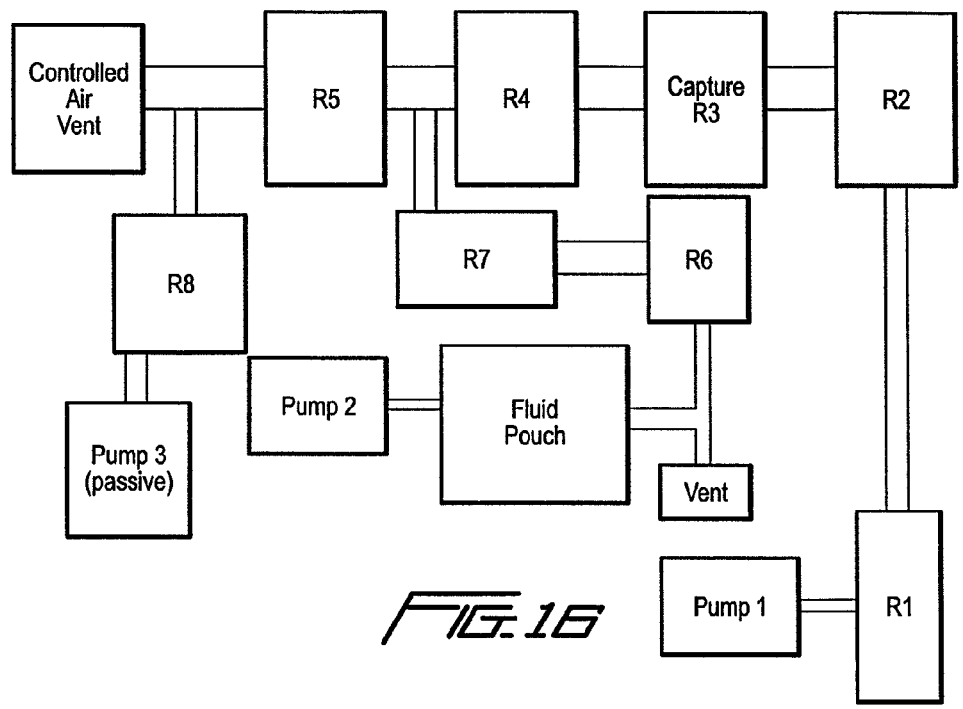
FIG. 16 is a schematic view of the fluidics of the preferred embodiment of an immunosensor cartridge.

Referring now to FIG. 16, there is shown a schematic view of the fluidics of the preferred embodiment of an immunosensor cartridge. Regions R1-R7 represent specific regions of the conduits associated with specific operational functions. Thus R1 represents the sample chamber; R2 the sample conduit whereby a metered portion of the sample is transferred to the capture region, and in which the sample is optionally amended with a substance coated upon the walls of the conduit; R3 represents the capture region, which houses the conductimetric and analyte sensors; R4 and R5 represent portions of the first conduit that are optionally used for further amendment of fluids with substances coated onto the conduit wall, whereby more complex assay schemes are achieved; R6 represents the portion of the second conduit into which fluid is introduced upon insertion of the cartridge into a reading apparatus; R7 comprises a portion of the conduit located between capillary stops 160 and 166, in which further amendment can occur; and R8 represents the portion of conduit 154 located between point 160 and vent 157, and which can further be used to amend liquids contained within.

Example 5

Coordination of Fluidics and Analyte Measurements

In the analysis sequence, a user places a sample into the cartridge, places the cartridge into the analyzer and in 1 to 20 minutes, a quantitative measurement of one or more analytes is performed. Herein is a non-limiting example of a sequence of events that occur during the analysis:

1) A 25 to 50 uL sample is introduced in the sample inlet 167 and fills to a capillary stop 151 formed by a 0.012" laser cut hole in the adhesive tape holding the cover and base components together. The user rotates a latex rubber disk mounted on a snap flap to close the sample inlet 167 and places the cartridge into the analyzer.

2) The analyzer makes contact with the cartridge, and a motor driven plunger presses onto the foil pouch 161 forcing the wash/analysis fluid out into a central conduit 158.

3) A separate motor driven plunger contacts the sample diaphragm 156 pushing a measured segment of the sample along the sample conduit (from reagent region R1 to R2). The sample is detected at the sensor chip 153 via the conductivity sensors. The sensor chip is located in capture region R3.

4) The sample is oscillated by means of the sample diaphragm 156 between R2 and R5 in a predetermined and controlled fashion for a controlled time to promote binding to the sensor.

5) The sample is pushed towards the waste region of the cartridge (R8) and comes in contact with a passive pump 157 in the form of a cellulose or similar absorbent wick. The action of wetting this wick seals the wick to air flow thus eliminating its ability to vent excess pressure generated by the sample diaphragm 156. The active vent becomes the "controlled air vent" of FIG. 16.

6) Rapid evacuation of the sample conduit (effected by withdrawing the motor driven plunger from the sample diaphragm 156) forces a mixture of air (from the vent) and wash/analysis fluid from the second conduit to move into the inlet located between R5 and R4 in FIG. 16. By repeating the rapid evacuation of the sample conduit, a series of air separated fluid segments are generated which are pulled across the sensor chip towards the sample inlet (from R4 to R3 to R2 and R1). This washes the sensor free of excess reagents and wets the sensor with reagents appropriate for the analysis. The wash/analysis fluid which originates in the foil pouch can be further amended by addition of reagents in R7 and R6 within the central wash/analysis fluid conduit.

7) The wash/analysis fluid segment is drawn at a slower speed towards the sample inlet to yield a sensor chip which contains only a thin layer of the analysis fluid. The electrochemical analysis is performed at this point. The preferred method of analysis is amperometry but potentiometry or impedance detection is also used.

8) And the mechanism retracts allowing the cartridge to be removed from the analyzer.

Figure 17:
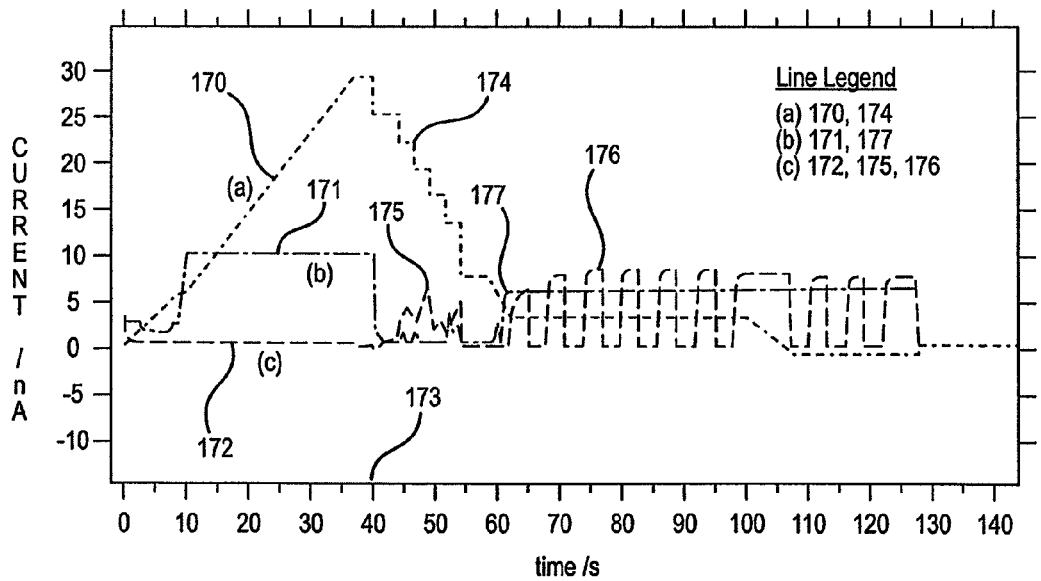
FIG. 17 illustrates the electrochemical response (current versus time), and other responses, of a preferred embodiment of an immunosensor.

Referring now to FIG. 17, there is illustrated an electrical signal 170 representing the position of the electric motor actuating the sample diaphragm 156, the response 171 of the conductimetric electrode, and the electrochemical response 172 of a amperometric immunosensor. In the time period prior to 40 seconds after initiation of the immunoassay 173, the motor depresses the diaphragm, which pushes the sample into the capture region and over the conductimetric sensor. Thus, after about 10 seconds, the conductivity rises to a steady value representative of sample filling the portion of the conduit containing the conductimetric sensor. During this period the valve is sealed by contact with the sample. Between 40 seconds and about 63 seconds, the motor position is stepped back in increments 174, creating a periodic fluctuation in pressure, which draws an air-segmented portion of wash fluid over the sensor. During this period, fluctuations 175 in the immunoassay sensor are seen. At 177, the conductimetric response indicates that the wash fluid, which contains substrate, covers the conductimetric sensor. As the fluid is drawn slowly over the sensor, a potential is applied (in this example, every five seconds, for 2.5 second periods) to the sensor, resulting in response 176, which indicates the presence of analyte bound to the sensor.

The invention described and disclosed herein has numerous benefits and advantages compared to previous devices. These benefits and advantages include, but are not limited to ease of use, the automation of most if not all steps of the analysis, which eliminates user included error in the analysis.

Example 6

In this example the amount of each component printed in the sample holding chamber in the base (coating) is shown. The components are BSA, glycine, methoxypolyethylene glycol, sucrose and bromophenol blue (used for quality control—may be viewed by some as a helpful "target"). The sample holding chamber in the base has to be corona treated in order to print. The base cocktail is very dilute and won't spread without a corona treatment). The cover is not required to be corona treated although it may be so treated in order to simplify operations. In a preferred embodiment there is no special treatment for the cover and no treatment around the orifice.

By way of example, the print cocktail may be made as follows. An aqueous solution of bromophenol blue is prepared (0.05 g in 10 g of deionized water). A reagent mixture is prepared by dissolving BSA (0.42 g), glycine (2.54 g), MePEG (0.39 g) and sucrose (1.4 g) in 250 mL of deionized water. The print cocktail used to print into the cartridge components constitutes reagent mixture (1.2 g), bromophenol blue solution (0.23 g) mixed with deionized water (53.4 g).
PT Base Cocktail Bromophenol Blue Solution

| | | |
|---|---|---|
| BBlue | | 0.05 g |
| Deionized water (DIW) | | 10 g |
| | | 0.005 g/g |

| PT Matrix | g | g/g |
|---|---|---|
| BSA | 0.4288 | 0.001715 |
| Glycine | 2.538 | 0.010152 |
| MePEG | 0.3938 | 0.001575 |
| Sucrose | 1.4 | 0.0056 |
| Total Volume | 250 | |

PT Base Print Cocktail: (g)

| | |
|---|---|
| DIW | 53.4 |
| PT matrix | 1.2 |
| BBlue Solution | 0.231 |
| Total | 54.831 |

| | (g) | g/g stock | g per component | base cocktail g/g | print 19ul g printed | ug printed |
|---|---|---|---|---|---|---|
| PT Matrix-BSA | 1.2 | 0.001715 | 0.00205824 | 3.75379E-05 | 7.1322E-07 | 0.71321989 |
| PT Matrix-Glycine | 1.2 | 0.010152 | 0.0121824 | 0.000222181 | 4.2214E-06 | 4.22143678 |
| PT Matrix-MePEG | 1.2 | 0.001575 | 0.00189024 | 3.44739E-05 | 6.55E-07 | 0.65500465 |
| PT Matrix-Sucrose | 1.2 | 0.0056 | 0.00672 | 0.000122558 | 2.3286E-06 | 2.32860973 |
| BBlue Solution | 0.231 | 0.005 | 0.001155 | 2.10647E-05 | 4.0023E-07 | 0.4002298 |

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

The invention claimed is:

1. An amperometric immunosensor, comprising:
   an electrochemical sensing surface for a blood sample having a porous polyvinyl alcohol layer patterned to cover at least a portion of the surface, and
   an antibody reagent layer disposed on the porous polyvinyl alcohol layer,
   wherein said porous polyvinyl alcohol layer attenuates background current from a blood sample to at least half the background current obtained in the absence of the porous polyvinyl alcohol layer.

2. The immunosensor of claim 1, wherein an antibody is attached to said porous polyvinyl alcohol layer on latex particles.

3. The immunosensor of claim 1, wherein the polyvinyl alcohol layer is patterned with a stilbizonium crosslinking agent and has a thickness 0.1 to 10 µm.

4. The immunosensor of claim 1, wherein the polyvinyl alcohol layer is patterned with a stilbizonium crosslinking agent and has a thickness from 0.5 to 5.0 µm.

5. The immunosensor of claim 1, wherein the polyvinyl alcohol layer is patterned with a stilbizonium crosslinking agent and has a thickness from 0.6 to 1.0 µm.

6. The immunosensor of claim 1, wherein the polyvinyl alcohol layer comprises bovine serum albumin.

7. The immunosensor of claim 1, wherein the polyvinyl alcohol layer is interposed between the electrochemical sensing surface and the antibody reagent layer.

8. The immunosensor of claim 1, wherein the polyvinyl alcohol layer comprises alkaline phosphatase.

9. The immunosensor of claim 1, wherein the antibody reagent layer is attached to microparticles that are dispensed onto the polyvinyl alcohol layer.

\* \* \* \* \*